United States Patent [19]

Schmidt et al.

[11] Patent Number: 4,539,579
[45] Date of Patent: Sep. 3, 1985

[54] COMPOUNDS, PROCESSES AND MARKING SYSTEMS

[75] Inventors: Paul J. Schmidt, Sharonville; William M. Hung, Cincinnati, both of Ohio

[73] Assignee: The Hilton-Davis Chemical Co., Cincinnati, Ohio

[21] Appl. No.: 439,382

[22] Filed: Nov. 5, 1982

[51] Int. Cl.$^3$ .............................................. B41M 5/20
[52] U.S. Cl. .................................. 346/218; 346/220; 346/223; 427/151
[58] Field of Search ........................ 204/2; 282/27.5; 428/411, 488, 537, 913, 914; 346/218, 220, 223

[56] References Cited

U.S. PATENT DOCUMENTS

| | | | |
|---|---|---|---|
| 3,974,041 | 8/1976 | Haruta et al. | 204/2 |
| 4,012,292 | 3/1977 | Fujiuara et al. | 204/2 |
| 4,017,366 | 4/1977 | Hsieh et al. | 346/200 |

FOREIGN PATENT DOCUMENTS

| | | | |
|---|---|---|---|
| 51-050327 | 5/1976 | Japan | 346/200 |
| 8089269 | 7/1980 | Japan | 346/200 |

OTHER PUBLICATIONS

Kuzuya, M.; Usui, T.; Ito, S.; Miyake, F.; Nozawa, S.; & Okuda, T., Chemical Pharmaceutical Bulletin, 1980, 28, (12), 3561–9.

*Primary Examiner*—Bruce H. Hess
*Attorney, Agent, or Firm*—Terrence E. Miesle; Paul E. Dupont; B. Woodrow Wyatt

[57] ABSTRACT

This invention relates to mono- and bis(aryl- and/or heteroaryl)-substituted-phthalazinones, phthalimidines, pyridopyridazinones and pyrrolopyridinones useful as color-forming substances, particularly in electrochromic recording systems, which are prepared by the interaction of a mono- or bis-substituted-phthalide or furopyridinone with a substituted or unsubstituted hydrazine.

16 Claims, No Drawings

COMPOUNDS, PROCESSES AND MARKING SYSTEMS

BACKGROUND OF THE INVENTION (a) Field of the Invention

This invention relates to novel compounds classified in the field of organic chemistry as phthalazinones, phthalimidines, pyridopyridazinones, and pyrrolopyridinones useful as color-forming substances, particularly in the art of electrochromic recording; to electrochromic recording systems containing as the color-forming substance said phthalazinones, phthalimidines, pyridopyridazinones and pyrrolopyridinones; and to processes for preparing the phthalazinones, phthalimidines, pyridopyridazinones and pyrrolopyridinones.

(b) Description of the Prior Art

Several classes of organic compounds of widely diverse structural types are known to be useful as colorless precursors for electrochromic recording. Among the more important classes, there may be named leuco type dyestuffs such as: phthalides, for example, crystal violet lactone, Malachite green lactone; fluorans, for example, 3-diethylamino-5,7-dimethylfluoran; and indolinobenzospiropyrans, for example, 1,3,3-trimethyl-6'-chloro-8'-methoxyindolinobenzospiropyran. Also utilized as colorless precursors for electrochromic recording, either alone or in admixture with the leuco compounds indicated above, are substances known as redox indicators. The redox indicator which becomes colored or discolored in situ in the electrochromic recording process also is generally a leuco body. Among the types of compounds which are applicable as redox indicators are phenothiazines, for example, leuco methylene blue and benzoyl leuco methylene blue. Other specific indicators are Leucoethyl Nile Blue, Leucomethyl Capryl Blue and Leucosafranine T. Typical of the many such electrochromic recording systems taught in the prior art are those described in U.S. Pat. Nos. 3,726,769, 3,871,972, 3,864,684, 4,017,366, 4,133,933, and U.S. Pat. No. Re. 29,427 which issued Apr. 10, 1973, Mar. 18, 1975, Feb. 4, 1975, Apr. 12, 1977, Jan. 9, 1979, and Oct. 4, 1977, respectively. The methods for electrochromic recording taught in the prior art have many variations. However, basically, one or both sides of a sheet of paper is coated or treated with a coating formulation containing at least one colorless color-forming (leuco) compound. Electrical current is then selectively applied to the coated side of the paper by some means, for example, a stylus or a printing head to which an electrical potential can be applied. The application of the current causes an electrochromic reaction, involving the leuco compound to produce a visible image corresponding to the design traced by the stylus or that of the printing head.

The following items to date appear to constitute the most relevant prior art with regard to the instant invention.

Kuzuya et al. in Chemical Pharmaceutical Bulletin 1980, 28(12), 3561-9 (C.A. 94:141182p) describe the preparation and physical characteristics of 4,4-diaryl-3,4-dihydro-1(2H)-phthalazinones having the structural formula

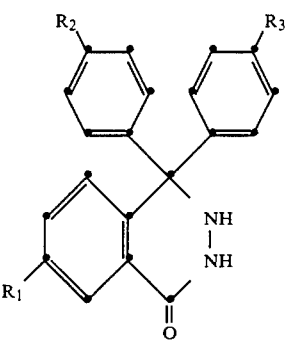

in which $R_1$ and $R_2$ are hydrogen or dimethylamino and $R_3$ is dimethylamino. These phthalazinones are prepared by interacting the corresponding phthalide with hydrazine hydrate in dilute aqueous ethyl alcohol. Although no utility for the compounds is given in the reference, it is taught that the compounds develop a weak green-blue color upon exposure to a weak mineral acid such as dilute hydrochloric acid or to bentonite. It is further stated that upon exposure to a strong acid the phthalazinones are converted to phthalimidines. The phthalazinones are said to show exceptional sensitivity to ultra-violet light and were found to be excellent initiators for photo-polymerization of unsaturated compounds.

Japanese Patent Publication No. 8,089,269, published July 5, 1980, discloses and claims phthalazinones having the structural formula

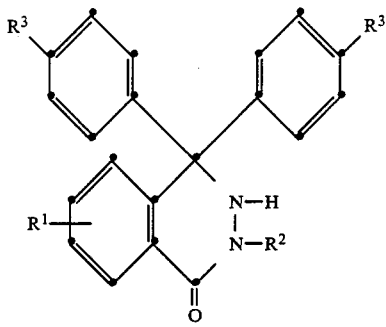

in which $R^1$ is hydrogen, lower alkylamino, lower alkyl, lower alkoxy or chlorine; $R^2$ is hydrogen or lower alkyl; and $R^3$ is lower alkylamino. The compounds are prepared by heating the corresponding phthalide with hydrazine hydrate. These phthalazinones are disclosed as photochemical initiators for photo-polymerization of unsaturated compounds.

U.S. Pat. No. 4,017,366, issued Apr. 12, 1977, discloses and claims a method of printing on thermographic paper according to which the heat for causing the imaging color change in the thermographic coating is generated by means of current in a portion of the coating dampened by a thin film of a conductive salt solution which is dispersed on the thermographic coating. The current is generated by a printing head having spaced electrodes in contact with the dampened portion of the coating.

Japanese Patent Publication No. 51,050,327, published May 1, 1976 discloses phenylhydrazinolactams having the structural formula

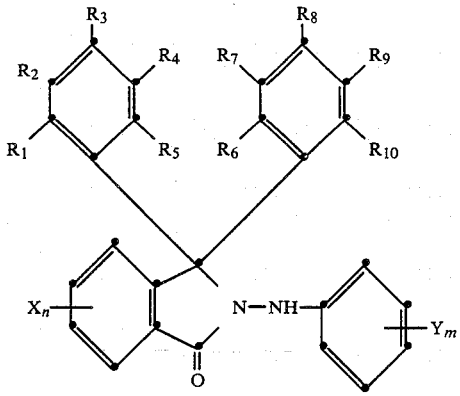

in which $R_1$ and $R_{10}$ represent hydrogen or lower alkyl; $R_2$ and $R_9$ represent hydrogen or lower alkyl; $R_3$ and $R_8$ represent lower monoalkylamino, lower dialkylamino, N-phenyl-N-lower alkylamino, dibenzylamino, or N-benzyl-N-lower alkylamino; $R_4$ and $R_7$ represent hydrogen, lower alkyl or halogen; $R_5$ and $R_6$ represent hydrogen, halogen, lower alkyl or alkoxy; n represents a number from 1 to 4; m represents a number from 1 to 5; X represents hydrogen, halogen, lower alkyl, lower monoalkylamino, lower dialkylamino or acylamino; and Y represents hydrogen, halogen or lower alkyl. The compounds are prepared by heating the corresponding phthalide with phenylhydrazine. No utility is disclosed for the phenylhydrazinolactams.

SUMMARY OF THE INVENTION

In its first composition of matter aspect, the invention relates to certain 3-$R^1$-4-X-4-Y-R-1(2H)-phthalazinones useful as colorless precursors in electrochromic recording systems.

In its second composition of matter aspect, the invention relates to certain isomeric mixtures of 7-$R^1$-8-X-8-Y-pyrido-[2,3d]-pyridazin-5(6H)-ones and 5-X-5-Y-6-$R^1$-pyrido-[2,3d]-pyridazin-8(5H)-ones useful as colorless precursors in electrochromic recording systems.

In its third composition of matter aspect, the invention relates to certain 2-(N-$R^1$-amino)-3-X-3-Y-R-phthalimidines useful as colorless precursors in electrochromic recording systems.

In a fourth composition of matter aspect, the invention relates to certain isomeric mixtures of 6-(N-$R^1$-amino)-7-X-7-Y-(5H)-pyrrolo-[3,4-b]-pyridin-5-ones and 5-X-5-Y-6-(N-$R^1$-amino)-(7H)-pyrrolo-[3,4-b]-pyridin-7-ones useful as colorless precursors in electrochromic recording systems.

The present invention provides in its first article of manufacture aspect, a substrate for use in electrochromic recording systems comprising a support sheet containing as a color-forming substance a 3-$R^1$-4-X-4-Y-phthalazin-1(2)-one.

The present invention provides in its second article of manufacture aspect, a substrate for use in electrochromic recording systems comprising a support sheet containing as a color-forming substance an isomeric mixture of 7-$R^1$-8-X-8-Y-pyrido-[2,3-d]-pyridazin-5(6H)-one and 5-X-5-Y-6-$R^1$-pyrido-[2,3d]-pyridazin-8(5H)-one.

The present invention provides in its third article of manufacture aspect, a substrate for use in electrochromic recording systems comprising a support sheet containing as a color-forming substance a 2-(N-$R^1$-amino)-3-X-3-Y-R-phthalimidine.

The present invention provides in its fourth article of manufacture aspect, a substrate for use in electrochromic recording systems a support sheet containing as a color-forming substance an isomeric mixture of 6-(N-$R^1$-amino)-7-X-7-Y-(5H)-pyrrolo-[3,4-b]-pyridin-5-one and 5-X-5-Y-6-(N-$R^1$-amino)-(7H)-pyrrolo-[3,4-b]-pyridin-7-one.

In its first process aspect, the invention relates to a process for producing a compound selected from the group of 3-$R^1$-4-X-4-Y-R-phthalazin-1(2H)-one and a 2-(N-$R^1$-amino)-3-X-3-Y-R-phthalimidine and mixtures thereof which comprises interacting the corresponding 3-X-3-Y-R-phthalide with the corresponding $R^1$ substituted hydrazine.

In its second process aspect, the invention relates to a process for producing a compound selected from the group consisting of an isomeric mixture of 7-$R^1$-8-X-8-Y-pyrido-[2,3-d]-pyridazin-5(6H)-one and 5-X-5-Y-6-$R^1$-pyrido-[2,3-d]-pyridazin-8(5H)-one; and an isomeric mixture of 6-(N-$R^1$-amino)-7-X-7-Y-(5H)-pyrrolo-[3,4-b]-pyridin-5-one and 5-X-5-Y-6-(N-$R^1$-amino)-[7H]-pyrrolo-[3,4-b]-pyridin-7-one which comprises interacting the corresponding isomeric mixture of 7-X-7-Y-furo-[2,3-b]-pyridin-7(5H)-one with the corresponding $R^1$ substituted hydrazine.

DETAILED DESCRIPTION INCLUSIVE OF THE PREFERRED EMBODIMENTS

More specifically, this invention in its first composition of matter aspect, resides in the novel 3-$R^1$-4-X-4-Y-R-dihydrophthalazin-1(2H)-ones which are particularly useful as colorless precursors in the art of electrochromic recording having the structural formula

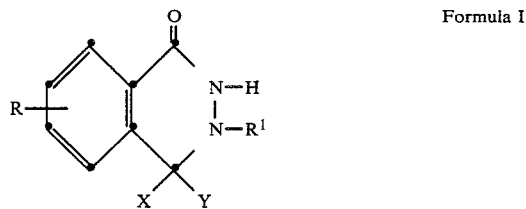

Formula I wherein: R represents hydrogen, dialkylamino in which alkyl is non-tertiary $C_1$ to $C_4$ alkyl, COOR² in which R² is hydrogen or non-tertiary $C_1$ to $C_{16}$ alkyl or one to four halo; $R^1$ is hydrogen, $C_1$ to $C_3$ alkyl, pyridyl, CZ in which Z is non-tertiary $C_1$ to $C_4$ alkoxy, $NHNH_2$ or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino; X is selected from the group consisting of

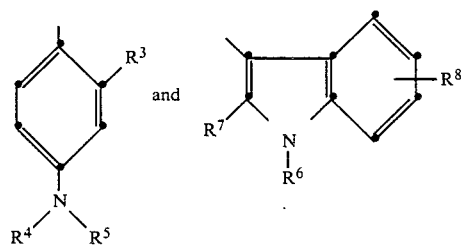

and and Y is selected from the group consisting of hydrogen,

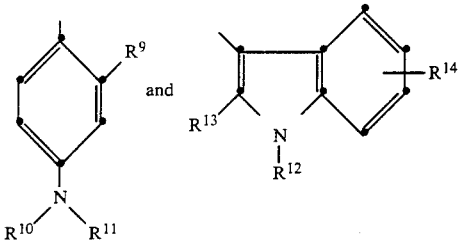

in which $R^3$ and $R^9$ independently represent hydrogen, non-tertiary $C_1$ to $C_4$ alkyl, non-tertiary $C_1$ to $C_4$ alkoxy, acylamino in which acyl is non-tertiary $C_2$ to $C_4$ alkyl or dialkylamino in which alkyl is non-tertiary $C_1$ to $C_4$ alkyl, $R^4$ and $R^{10}$ independently represent non-tertiary $C_1$ to $C_4$ alkyl, benzyl or benzyl substituted in the benzene ring by one or two of halo or $C_1$ to $C_3$ alkyl, $R^5$ and $R^{11}$ independently represent non-tertiary $C_1$ to $C_4$ alkyl, benzyl or benzyl substituted in the benzene ring by one or two of halo or $C_1$ to $C_3$ alkyl, $R^6$ and $R^{12}$ independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or non-tertiary $C_1$ to $C_4$ alkyl, $R^7$ and $R^{13}$ independently represent hydrogen, $C_1$ to $C_3$ alkyl or phenyl, and $R^8$ and $R^{14}$ independently represent hydrogen, halo, non-tertiary $C_1$ to $C_4$ alkyl, non-tertiary $C_1$ to $C_4$ alkoxy or nitro with the proviso that when $R^3$ and $R^9$ are both hydrogen, $R^4$, $R^5$, $R^{10}$ and $R^{11}$ can not simultaneously be non-tertiary $C_1$ to $C_4$ alkyl.

Preferred compounds within the ambit of the first composition of matter aspect are the novel 3-$R^1$-4-Y-4-(2-$R^3$-4-N-$R^4$-N-$R^5$-aminophenyl)-R-phthalazin-1(2H)-ones of Formula I wherein X is 2-$R^3$-4-N-$R^4$-N-$R^5$-aminophenyl having the structural formula

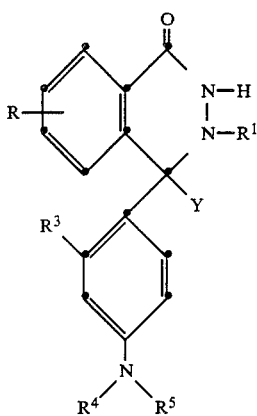

Formula II in which R, $R^1$, $R^3$, $R^4$, $R^5$ and Y each have the same respective meanings given in Formula I; the novel 3-$R^1$-4-[2-$R^3$-4-(N-$R^4$-N-$R^5$-amino)phenyl]-4-[2-$R^9$-4-(N-$R^{10}$-N-$R^{11}$-amino)phenyl]-R-phthalazin-1(2H)-ones of Formula I wherein X is 2-$R^3$-4-(N-$R^4$-N-$R^5$-amino)phenyl and Y is 2-$R^9$-4-(N-$R^{10}$-N-$R^{11}$-amino)phenyl having the structural formula

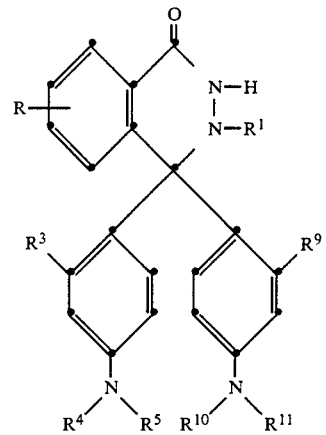

Formula III in which R, $R^1$, $R^3$, $R^4$, $R^5$, $R^9$, $R^{10}$ and $R^{11}$ each have the same respective meanings given in Formula II; the novel 3-$R^1$-4-[2-$R^3$-4-(N-$R^4$-N-$R^5$-amino)phenyl]-4-(1-$R^{12}$-2-$R^{13}$-5/6-$R^{14}$-indol-3-yl)-R-phthalazin-1(2H)-ones of Formula I wherein X is 2-$R^3$-4-(N-$R^4$-N-$R^5$-amino)phenyl and Y is 1-$R^{12}$-2-$R^{13}$-5/6-$R^{14}$-indol-3-yl having the structural formula

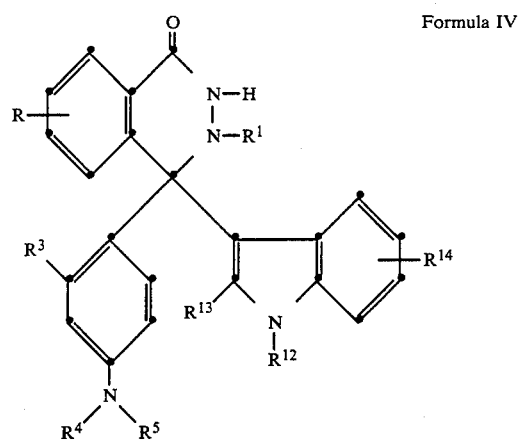

Formula IV in which R, $R^1$, $R^3$, $R^4$, $R^5$, $R^{12}$, $R^{13}$ and $R^{14}$ each have the same respective meanings given in Formula I; and the novel 3-$R^1$-4-(1-$R^6$-2-$R^7$-5/6-$R^8$-indol-3-yl)-4-(1-$R^{12}$-2-$R^{13}$-5/6-$R^{14}$-indol-3-yl)-R-phthalazin-1(2H)-ones of Formula I wherein X is 1-$R^6$-2-$R^7$-5/6-$R^8$-indol-3-yl and Y is 1-$R^{12}$-2-$R^{13}$-5/6-$R^{14}$-indol-3-yl having the structural formula

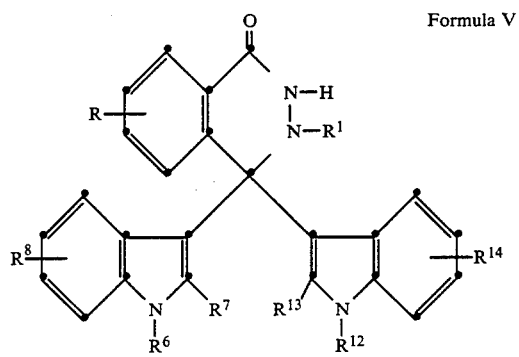

Formula V in which R, $R^1$, $R^6$, $R^7$, $R^8$, $R^{12}$, $R^{13}$ and $R^{14}$ each have the same respective meanings given in Formula I.

In a second composition of matter aspect, the invention sought to be patented resides in the novel isomeric mixture of 7-$R^1$-8-X-8-Y-pyrido-[2,3-d]-pyridazin-5(6H)-ones and 5-X-5-Y-6-$R^1$-pyrido-[2,3-d]-pyridazin-8(5H)-ones having the structural formulas, respectively

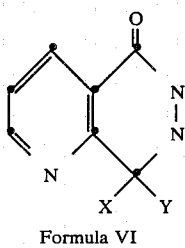 and 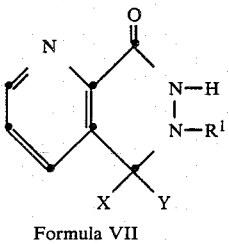

Formula VI        Formula VII wherein: $R^1$ is hydrogen, $C_1$ to $C_3$ alkyl, pyridyl,

in which Z is non-tertiary $C_1$ to $C_4$ alkoxy, $NHNH_2$ or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino; X is selected from the group consisting of

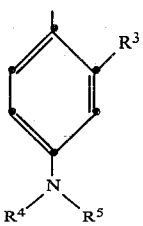 and 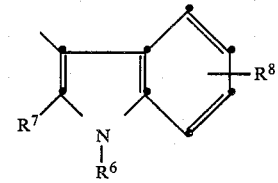

and Y is selected from the group consisting of hydrogen,

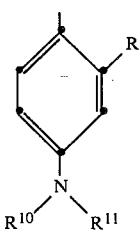 and 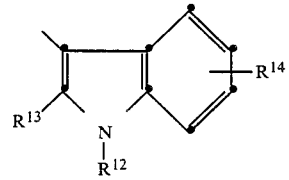

in which $R^3$ and $R^9$ independently represent hydrogen, non-tertiary $C_1$ to $C_4$ alkyl, non-tertiary $C_1$ to $C_4$ alkoxy, acylamino in which acyl is non-tertiary $C_2$ to $C_4$ alkyl or dialkylamino in which alkyl is non-tertiary $C_1$ to $C_4$ alkyl, $R^4$ and $R^{10}$ independently represent non-tertiary $C_1$ to $C_4$ alkyl, benzyl or benzyl substituted in the benzene ring by one or two of halo or $C_1$ to $C_3$ alkyl, $R^5$ and $R^{11}$ indenpendently represent non-tertiary $C_1$ to $C_4$ alkyl, benzyl or benzyl substituted in the benzene ring by one or two of halo or $C_1$ to $C_3$ alkyl, $R^6$ and $R^{12}$ independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or non-tertiary $C_1$ to $C_4$ alkyl, $R^7$ and $R^{13}$ independently represent hydrogen, $C_1$ to $C_3$ alkyl or phenyl, and $R^8$ and $R^{14}$ independently represent hydrogen, halo, non-tertiary $C_1$ to $C_4$ alkyl, non-tertiary $C_1$ to $C_4$ alkoxy or nitro.

Preferred compounds within the ambit of the second composition of matter aspect are the novel isomeric mixtures of 7-$R^1$-8-[2-$R^3$-4-(N-$R^4$-N-$R^5$-amino)phenyl]-8-(1-$R^{12}$-2-$R^{13}$-5/6-$R^{14}$-indol-3-yl)-pyrido-[2,3-d]-pyridazin-5(6H)-one and 5-(2-$R^3$-4-N-$R^4$-N-$R^5$-aminophenyl)-5-(1-$R^{12}$-2-$R^{13}$-5/6-$R^{14}$-indol-3-yl)-6-$R^1$-pyrido-[2,3-d]-pyridazin-8(5H)-ones having the structural formulas, respectively

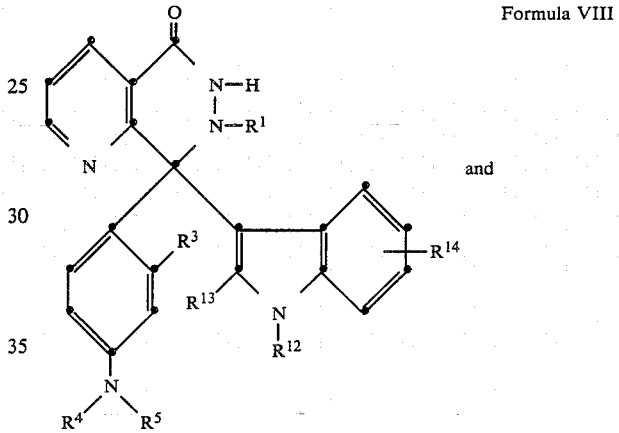

Formula VIII and

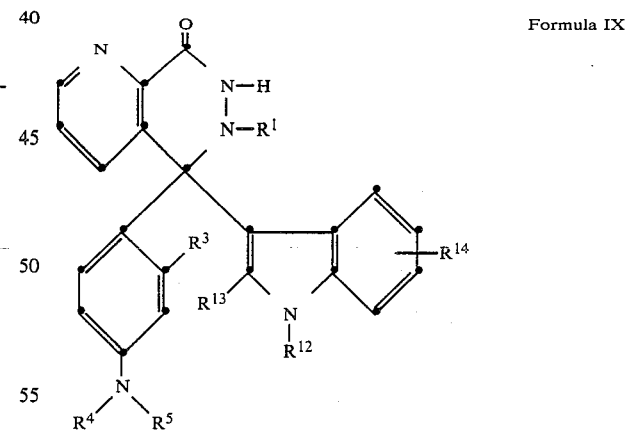

Formula IX in which $R^1$, $R^3$, $R^4$, $R^5$, $R^{12}$, $R^{13}$ and $R^{14}$ each have the same respective meanings given in Formulas VI and VII; and the novel isomeric mixture of 7-$R^1$-8-(1-$R^6$-2-$R^7$-5/6-$R^8$-indol-3-yl)-8-(1-$R^{12}$-2-$R^{13}$-5/6-$R^{14}$-indol-3-yl)-pyrido-[2,3-d]-pyridazin-5(6H)-one and 5-(1-$R^6$-2-$R^7$-5/6-$R^8$-indol-3-yl)-5-(1-$R^{12}$-2-$R^{13}$-5/6-$R^{14}$-indol-3-yl)-6-$R^1$-pyrido-[2,3-d]-pyridazin-8(5H)-one having the structural formulas, respectively

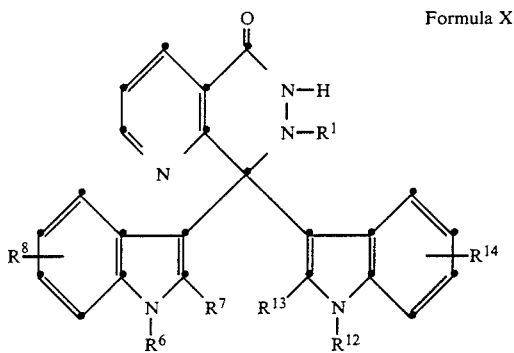

Formula X and

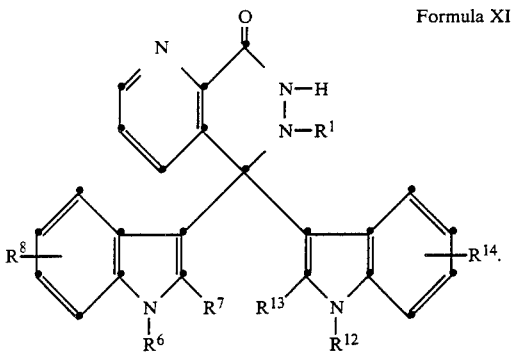

Formula XI in which $R^1$, $R^6$, $R^7$, $R^8$, $R^{12}$, $R^{13}$ and $R^{14}$ each have the same respective meanings given in Formulas VI and VII.

In a third composition of matter aspect, the invention sought to be patented resides in the novel 2-(N-$R^1$-amino)-3-X-3-Y-R-phthalimidines having the formula

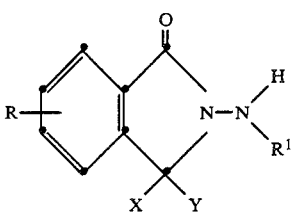

Formula XII wherein: R represents hydrogen, dialkylamino in which alkyl is non-tertiary $C_1$ to $C_4$ alkyl, COO$R^2$ in which $R^2$ is hydrogen or non-tertiary $C_1$ to $C_{16}$ alkyl or one to four halo; $R^1$ represents hydrogen, $C_1$ to $C_3$ alkyl, pyridyl,

CZ in which Z is non-tertiary $C_1$ to $C_4$ alkoxy, NHNH$_2$ or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino; X is selected from the group consisting of and Y is selected from the group consisting of hydrogen, in which $R^3$ and $R^9$ independently represent hydrogen, non-tertiary $C_1$ to $C_4$ alkyl, non-tertiary $C_1$ to $C_4$ alkoxy, acylamino in which acyl is non-tertiary $C_2$ to $C_4$ alkyl or dialkylamino in which alkyl is non-tertiary $C_1$ to $C_4$ alkyl, $R^4$ and $R^{10}$ independently represent non-tertiary $C_1$ to $C_4$ alkyl, benzyl or benzyl substituted in the benzene ring by one or two of halo or $C_1$ to $C_3$ alkyl, $R^5$ and $R^{11}$ independently represent non-tertiary $C_1$ to $C_4$ alkyl, benzyl or benzyl substituted in the benzene ring by one or two of halo or $C_1$ to $C_3$ alkyl, $R^6$ and $R^{12}$ independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or non-tertiary $C_1$ to $C_4$ alkyl, $R^7$ and $R^{13}$ independently represent hydrogen, $C_1$ to $C_3$ alkyl or phenyl, and $R^8$ and $R^{14}$ independently represent hydrogen, halo, non-tertiary $C_1$ to $C_4$ alkyl, non-tertiary $C_1$ to $C_4$ alkoxy or nitro with the proviso that when $R^3$ and $R^9$ are both hydrogen, $R^4$, $R^5$, $R^{10}$ and $R^{11}$ can not simultaneously be non-tertiary $C_1$ to $C_4$ alkyl.

Preferred compounds within the ambit of the third composition of matter aspect are the novel 2-(N-$R^1$-amino)-3-[2-$R^3$-4-(N-$R^4$-N-$R^5$-amino)phenyl]-3-Y-5/6-R-phthalimidines having the structural formula Formula XIII

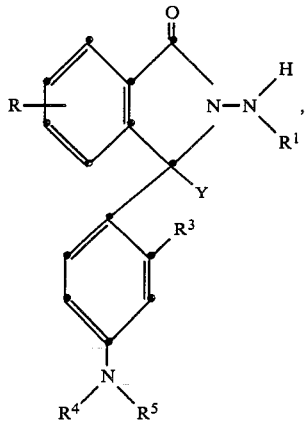

in which R, $R^1$, $R^3$, $R^4$, $R^5$ and Y each have the same respective meanings given in Formula XII; the novel 2-(N-$R^1$-amino)-3-[2-$R^3$-4-N-($R^4$-N-$R^5$-amino)phenyl]-3-(2-$R^9$-4-N-$R^{10}$-N-$R^{11}$-aminophenyl)-5/6-R-phthalimidines having the structural formula Formula XIV

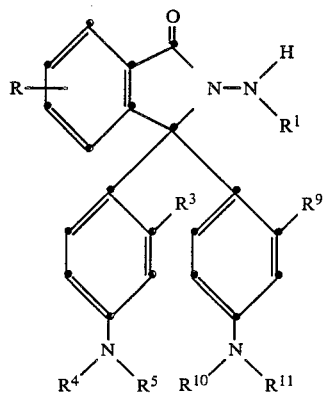

in which R, $R^1$, $R^3$, $R^4$, $R^5$, $R^9$, $R^{10}$ and $R^{11}$ each have the same respective meanings given in Formula XII; the novel 2-(N-$R^1$-amino)-3-[2-$R^3$-4-(N-$R^4$-N-$R^5$-amino)phenyl]-3-(1-$R^{12}$-2-$R^{13}$-5/6-$R^{14}$-indol-3-yl)-5/6-R-phthalimidines having the structural formula Formula XV

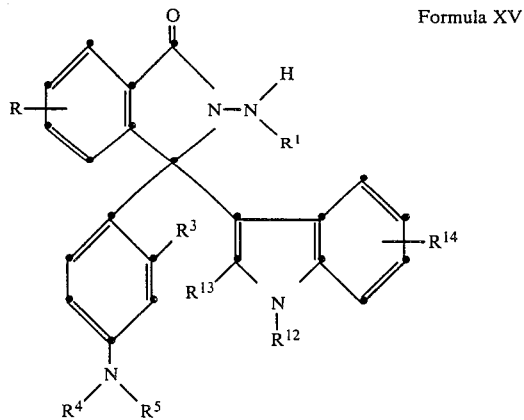

in which R, $R^1$, $R^3$, $R^4$, $R^5$, $R^{12}$, $R^{13}$ and $R^{14}$ each have the same respective meanings given in Formula XII; and the novel 2-(N-$R^1$-amino)-3-(1-$R^6$-2-$R^7$-5/6-$R^8$-indol-3-yl)-3-(1-$R^{12}$-2-$R^{13}$-5/6-$R^{14}$-indol-3-yl)-5/6-R-phthalimidine having the structural formula Formula XVI

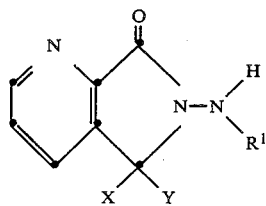

in which R, $R^1$, $R^6$, $R^7$, $R^8$, $R^{12}$, $R^{13}$ and $R^{14}$ each have the same respective meanings given in Formula XII.

In a fourth composition of matter aspect, the invention sought to be patented resides in the novel isomeric mixtures of compounds having the structural formulas Formula XVII

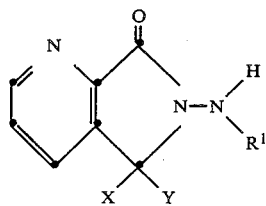

and

Formula XVIII wherein: $R^1$ is hydrogen, $C_1$ to $C_3$ alkyl, pyridyl, $$\overset{O}{\underset{}{\parallel}}_{CZ}$$

in which Z is non-tertiary $C_1$ to $C_4$ alkoxy, $NHNH_2$ or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino; X is selected from the group consisting of

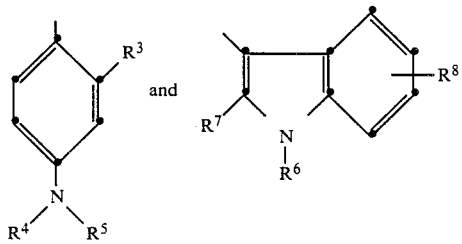

and and Y is selected from the group consisting of hydrogen,

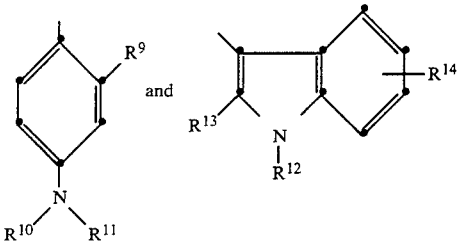

in which $R^3$ and $R^9$ independently represent hydrogen, non-tertiary $C_1$ to $C_4$ alkyl, non-tertiary $C_1$ to $C_4$ alkoxy, acylamino in which acyl is non-tertiary $C_2$ to $C_4$ alkyl or dialkylamino in which alkyl is non-tertiary $C_1$ to $C_4$ alkyl, $R^4$ and $R^{10}$ independently represent non-tertiary $C_1$ to $C_4$ alkyl, benzyl or benzyl substituted in the benzene ring by one or two of halo or $C_1$ to $C_3$ alkyl, $R^5$ and $R^{11}$ independently represent non-tertiary $C_1$ to $C_4$ alkyl, benzyl or benzyl substituted in the benzene ring by one or two of halo or $C_1$ to $C_3$ alkyl, $R^6$ and $R^{12}$ independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or non-tertiary $C_1$ to $C_4$ alkyl, $R^7$ and $R^{13}$ independently represent hydrogen, $C_1$ to $C_3$ alkyl or phenyl, and $R^8$ and $R^{14}$ independently represent hydrogen, halo, non-tertiary $C_1$ to $C_4$ alkyl, non-tertiary $C_1$ to $C_4$ alkoxy or nitro.

Preferred compounds within the ambit of the fourth composition of the matter aspect are the novel isomeric mixtures of 6-(N-$R^1$-amino)-7-[2-$R^3$-4-(N-$R^4$-N-$R^5$-amino)phenyl]-7-(1-$R^{12}$-2-$R^{13}$-5/6-$R^{14}$-indol-3-yl)-(5H)-pyrrolo-[3,4-b]-pyridin-5-ones and 5-[2-$R^3$-4-(N-$R^4$-N-$R^5$-amino)phenyl]-5-(1-$R^{12}$-2-$R^{13}$-5/6-$R^{14}$-indol-3-yl)-6-(N-$R^1$-amino)-(7H)-pyrrolo-[3,4-b]-pyridin-7-ones having the structural formulas

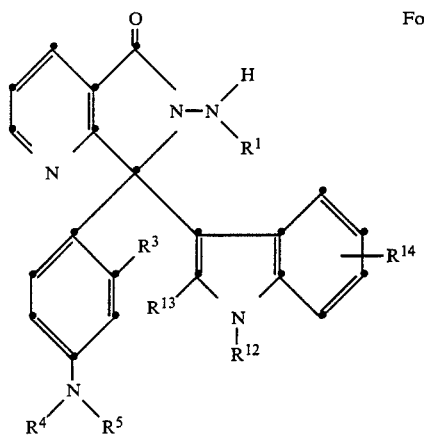

Formula XIX

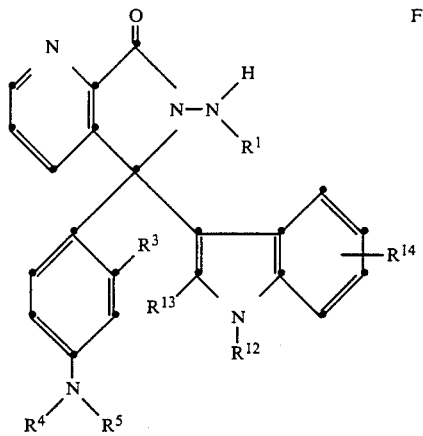

Formula XX in which $R^1$, $R^3$, $R^4$, $R^5$, $R^{12}$, $R^{13}$ and $R^{14}$ each have the same respective meanings given in Formulas XVII and XVIII; and the novel isomeric mixtures of 6-(N-$R^1$-amino)-7-(1-$R^6$-2-$R^7$-5/6-$R^8$-indol-3-yl)-7-(1-$R^{12}$-2-$R^{13}$-5/6-$R^{14}$-indol-3-yl)-(5H)-pyrrolo-[3,4-b)-pyridin-5-ones and 5-(1-$R^6$-2-$R^7$-5/6-$R^8$-indol-3-yl)-5-(1-$R^{12}$-2-$R^{13}$-5/6-$R^{14}$-indol-3-yl)-6-(N-$R^1$-amino)-(7H)-pyrrolo-[3,4-b]-pyridin-7-ones having the structural formulas

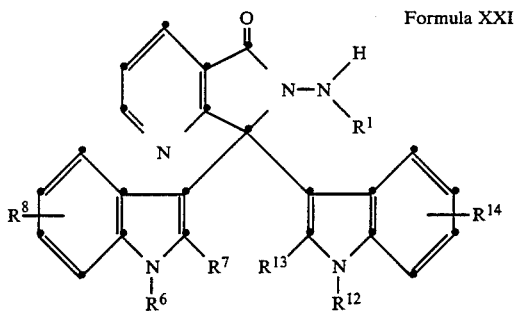

Formula XXI

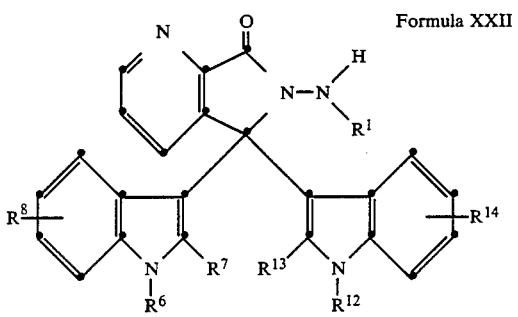

Formula XXII in which R, $R^1$, $R^6$, $R^7$, $R^8$, $R^{12}$, $R^{13}$ and $R^{14}$ each have the same respective meanings given in Formulas XVII and XVIII.

In the first of its article of manufacture aspects, the invention sought to be patented resides in a substrate for use in electrochromic recording comprising a support sheet containing as a color-forming substance a 3-$R^1$-4-X-4-Y-R-phthalazin-1(2H)-one having the structural formula

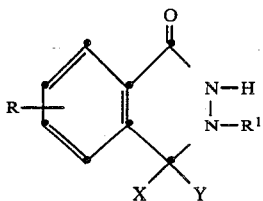

Formula I wherein: R represents hydrogen, dialkylamino in which alkyl is non-tertiary $C_1$ to $C_4$ alkyl, $COOR^2$ in which $R^2$ is hydrogen or non-tertiary $C_1$ to $C_{16}$ alkyl or one to four halo; $R^1$ is hydrogen, $C_1$ to $C_3$ alkyl, pyridyl,

in which Z is non-tertiary $C_1$ to $C_4$ alkoxy, $NHNH_2$ or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino; X is selected from the group consisting of

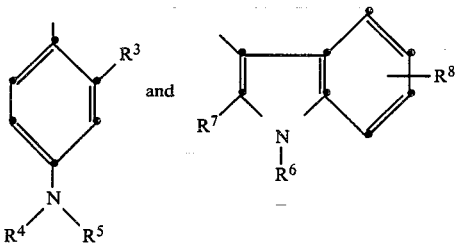

and Y is selected from the group consisting of hydrogen,

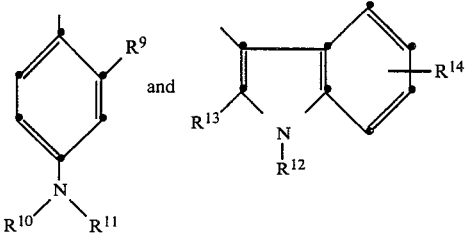

in which $R^3$ and $R^9$ independently represent hydrogen, non-tertiary $C_1$ to $C_4$ alkyl, non-tertiary $C_1$ to $C_4$ alkoxy, acylamino in which acyl is non-tertiary $C_2$ to $C_4$ alkyl or dialkylamino in which alkyl is non-tertiary $C_1$ to $C_4$ alkyl, $R^4$ and $R^{10}$ independently represent non-tertiary $C_1$ to $C_4$ alkyl, benzyl or benzyl substituted in the benzene ring by one or two of halo or $C_1$ to $C_3$ alkyl, $R^5$ and $R^{11}$ independently represent non-tertiary $C_1$ to $C_4$ alkyl, benzyl or benzyl substituted in the benzene ring by one or two of halo or $C_1$ to $C_3$ alkyl, $R^6$ and $R^{12}$ independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or non-tertiary $C_1$ to $C_4$ alkyl, $R^7$ and $R^{13}$ independently represent hydrogen, $C_1$ to $C_3$ alkyl or phenyl, and $R_8$ and $R^{14}$ independently represent hydrogen, halo, non-tertiary $C_1$ to $C_4$ alkyl, non-tertiary $C_1$ to $C_4$ alkoxy or nitro.

Preferred articles within the ambit of first article of manufacture are those wherein the color-forming component comprises a 3-$R^1$-4-Y-4-[2-$R^3$-4-(N-$R^4$-N-$R^5$-amino)-phenyl]-6/7-R-phthalazin-1(2H)-one of Formula II wherein R, $R^1$, $R^3$, $R^4$, $R^5$ and Y each have the same respective meanings given in Formula I; a 3-$R^1$-[2-$R^3$-4-(N-$R^4$-N-$R^5$-amino)phenyl]-4-[2-$R^9$-4-(N-$R^{10}$-N-$R^{11}$-amino)phenyl]-6/7-R-phthalazin-1(2H)-one of Formula III wherein R, $R^1$, $R^3$, $R^4$, $R^5$, $R^9$, $R^{10}$ and $R^{11}$ each have the same respective meanings given in Formula I; a 3-$R^1$-4-[2-$R^3$-4-(N-$R^4$-N-$R^5$-amino)phenyl]-4-(1-$R^{12}$-2-$R^{13}$-5/6-$R^{14}$-indol-3-yl)-6/7-R-phthalazin-1(2H)-one of Formula IV wherein R, $R^1$, $R^3$, $R^4$, $R^5$, $R^{12}$, $R^{13}$ and $R^{14}$ each have the same respective meanings given in Formula I; and a 3-$R^1$-4-(1-$R^6$-2-$R^7$-5/6-$R^8$-indol-3-yl)-4-(1-$R^{12}$-2-$R^{13}$-5/6-$R^{14}$-indol-3-yl)-6/7-R-phthalazin-1(2H)-one of Formula V wherein R, $R^1$, $R^6$, $R^7$, $R^8$, $R^{12}$, $R^{13}$ and $R^{14}$ each have the same respective meanings given in Formula I.

In a second article of manufacture aspect, the invention sought to be patented resides in the novel substrate for use in electrochromic recording containing as a color-forming substance an isomeric mixture of 7-$R^1$-8-X-8-Y-pyrido-[2,3-d]-pyridazin-5(6H)-ones of Formula VI and 5-X-5-Y-6-$R^1$-pyrido-[2,3-d]-pyridazin-8(5H)-ones of Formula VII having the structural formulas, respectively

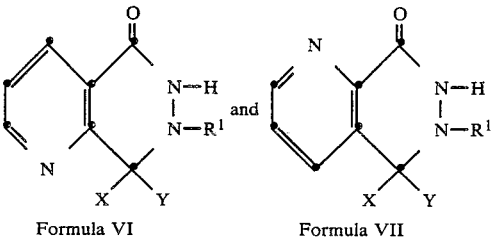

Formula VI          Formula VII wherein: $R^1$ is hydrogen, $C_1$ to $C_3$ alkyl, pyridyl,

in which Z is non-tertiary $C_1$ to $C_4$ alkoxy, $NHNH_2$ or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino; X is selected from the group consisting of

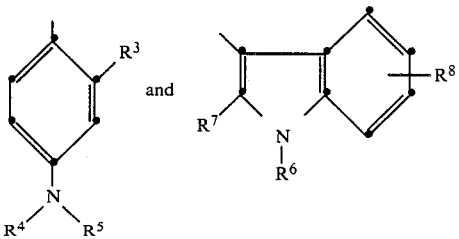

and Y is selected from the group consisting of hydrogen,

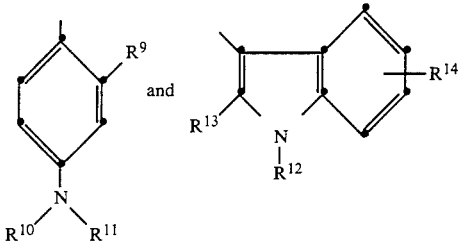

in which $R^3$ and $R^9$ independently represent hydrogen, non-tertiary $C_1$ to $C_4$ alkyl, non-tertiary $C_1$ to $C_4$ alkoxy, acylamino in which acyl is non-tertiary $C_2$ to $C_4$ alkyl or dialkylamino in which alkyl is non-tertiary $C_1$ to $C_4$ alkyl, $R^4$ and $R^{10}$ independently represent non-tertiary $C_1$ to $C_4$ alkyl, benzyl or benzyl substituted in the benzene ring by one or two of halo or $C_1$ to $C_3$ alkyl, $R^5$ and $R^{11}$ independently represent non-tertiary $C_1$ to $C_4$ alkyl, benzyl or benzyl substituted in the benzene ring by one or two or halo or $C_1$ to $C_3$ alkyl, $R^6$ and $R^{12}$ independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or non-tertiary $C_1$ to $C_4$ alkyl, $R^7$ and $R^{13}$ independently represent hydrogen, $C_1$ to $C_3$ alkyl or phenyl, and $R^8$ and $R^{14}$ independently represent hydrogen, halo, non-tertiary $C_1$ to $C_4$ alkyl, non-tertiary $C_1$ to $C_4$ alkoxy or nitro.

Preferred articles within the ambit of the second article of manufacture are those wherein the color-forming component comprises an isomeric mixture of 7-$R^1$-8-[2-$R^3$-4-(N-$R^4$-N-$R^5$-amino)phenyl]-8-(1-$R^{12}$-2-$R^{13}$-5/6-$R^{14}$-indol-3-yl)-pyrido-[2,3-d]-pyridazin-5(6H)-ones of Formula VIII and 5-[2-$R^3$-4-(N-$R^4$-N-$R^5$-amino)phenyl]-5-(1-$R^{12}$-2-$R^{13}$-5/6-$R^{14}$-indol-3-yl)-pyrido-[2,3-d]-pyridazin-8(5H)-ones of Formula IX in which $R^1$, $R^3$, $R^4$, $R^5$, $R^{12}$, $R^{13}$ and $R^{14}$ each have the same respective meanings given in Formulas VI and VII; and an isomeric mixture of 7-$R^1$-8-(1-$R^6$-2-$R^7$-5/6-$R^8$-indol-3-yl)-8-(1-$R^{12}$-2-$R^{13}$-5/6-$R^{14}$-indol-3-yl)-pyrido-[2,3-d]-pyridazin-5(6H)-ones of Formula X and 5-(1-$R^6$-2-$R^7$-5/6-$R^8$-indol-3-yl)-5-(1-$R^{12}$-2-$R^{13}$-5/6-$R^{14}$-indol-3-yl)-6-$R^1$-pyrido-[2,3-d]-pyridazin-8(5H)-ones of Formula XII in which $R^1$, $R^6$, $R^7$, $R^8$, $R^{12}$, $R^{13}$ and $R^{14}$ each have the same respective meanings given in Formulas VI and VII.

In a third article of manufacture aspect, the invention sought to be patented resides in the novel substrate for use in electrochromic recording containing as a color-forming substance the novel 2-(N-$R^1$-amino)-3-X-3-Y-R-phthalimidines of Formula XII having the formula

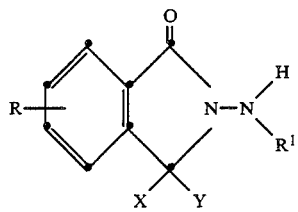

Formula XII wherein: R represents hydrogen, dialkylamino in which alkyl is non-tertiary $C_1$ to $C_4$ alkyl, COOR$^2$ in which $R^2$ is hydrogen or non-tertiary $C_1$ to $C_{16}$ alkyl or one to four halo; $R^1$ represents hydrogen, $C_1$ to $C_3$ alkyl, pyridyl,

in which Z is non-tertiary $C_1$ to $C_4$ alkoxy, NHNH$_2$ or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino; X is selected from the group consisting of

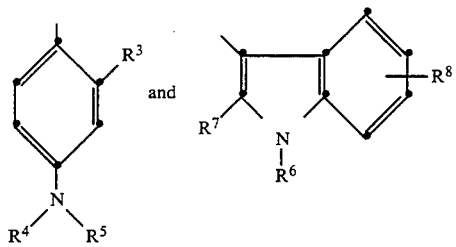

and Y is selected from the group consisting of hydrogen,

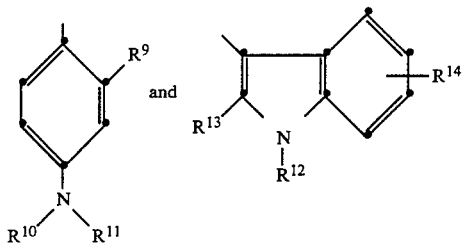

in which $R^3$ and $R^9$ independently represent hydrogen, non-tertiary $C_1$ to $C_4$ alkyl, non-tertiary $C_1$ to $C_4$ alkoxy, acylamino in which acyl is non-tertiary $C_2$ to $C_4$ alkyl or dialkylamino in which alkyl is non-tertiary $C_1$ to $C_4$ alkyl, $R^4$ and $R^{10}$ independently represent non-tertiary $C_1$ to $C_4$ alkyl, benzyl or benzyl substituted in the benzene ring by one or two of halo or $C_1$ to $C_3$ alkyl, $R^5$ and $R^{11}$ independently represent non-tertiary $C_1$ to $C_4$ alkyl, benzyl or benzyl substituted in the benzene ring by one or two of halo or $C_1$ to $C_3$ alkyl, $R^6$ and $R^{12}$ independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or non-tertiary $C_1$ to $C_4$ alkyl, $R^7$ and $R^{13}$ independently represent hydrogen, $C_1$ to $C_3$ alkyl or phenyl, and $R^8$ and $R^{14}$ independently represent hydrogen, halo, non-tertiary $C_1$ to $C_4$ alkyl, non-tertiary $C_1$ to $C_4$ alkoxy or nitro with the proviso that when $R^3$ and $R^9$ are both hydrogen, $R^4$, $R^5$, $R^{10}$ and $R^{11}$ can not simultaneously be non-tertiary $C_1$ to $C_4$ alkyl.

Preferred articles within the third article of manufacture aspect are those wherein the color-forming component comprises a 2-(N-$R^1$-amino)-3-[2-$R^3$-4-(N-$R^4$-N-$R^5$-amino)phenyl]-3-Y-R-phthalimidine of Formula XIII in which R, $R^1$, $R^3$, $R^4$, $R^5$ and Y each have the same respective meanings given in Formula XII; a 2-(N-$R^1$-amino)-3-[2-$R^3$-4-(N-$R^4$-N-$R^5$-amino)phenyl]-3-[2-$R^9$-4-(N-$R^{10}$-N-$R^{11}$-amino)phenyl]-R-phthalimidine of Formula XIV in which R, $R^1$, $R^3$, $R^4$, $R^5$, $R^9$, $R^{10}$ and $R^{11}$ each have the same respective meanings given in Formula XII; a 2-(N-R$^1$-amino)-3-[2-R$^3$-4-(N-R$^4$-(N-R$^5$-amino)-phenyl]-3-(1-R$^{12}$-2-R$^{13}$-5/6-R$^{14}$-indol-3-yl)-R-phthalimidine of Formula XV in which R, R$^1$, R$^4$, R$^5$, R$^6$, R$^{12}$, R$^{13}$ and R$^{14}$ each have the same respective meanings given in Formula XIV; and a 2-(N-R$^1$-amino)-3-(1-R$^6$-2-R$^7$-5/6-R$^8$-indol-3-yl)-3-(1-R$^{12}$-2-R$^{13}$-5/6-R$^{14}$-indol-3-yl)-R-phthalimidine of Formula XVI in which R, R$^1$, R$^6$, R$^7$, R$^8$, R$^{12}$, R$^{13}$ and R$^{14}$ each have the same respective meanings given in Formula XII.

In a fourth article of manufacture aspect, the invention sought to be patented resides in the novel substrate for use in electrochromic recording containing as a color-forming substance the novel isomeric mixtures of 6-(N-R$^1$-amino)-7-X-7-Y-(5H)-pyrrolo-[3,4-b]-pyridin-5-ones of Formula XVII and 5-X-5-Y-6-(N-R$^1$-amino)-(7H)-pyrrolo-[3,4-b]-pyridin-7-ones of Formula XVIII having the structural formulas

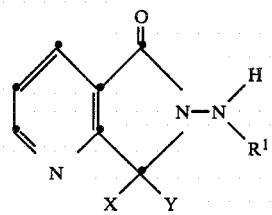

Formula XVII and

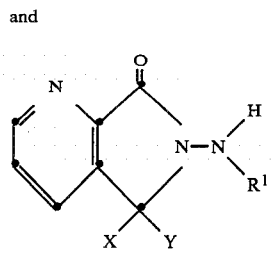

Formula XVIII wherein: R$^1$ is hydrogen, C$_1$ to C$_3$ alkyl, pyridyl,

in which Z is non-tertiary C$_1$ to C$_4$ alkoxy, NHNH$_2$ or non-tertiary C$_1$ to C$_4$ alkyl, phenyl or phenyl substituted by one or two of C$_1$ to C$_3$ alkyl, non-tertiary C$_1$ to C$_4$ alkoxy, halo, nitro or amino; X is selected from the group consisting of

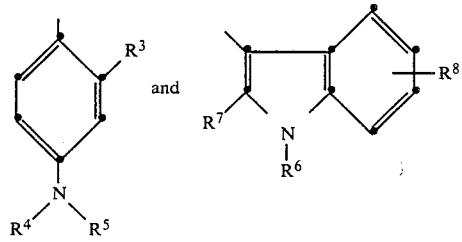

and Y is selected from the group consisting of hydrogen,

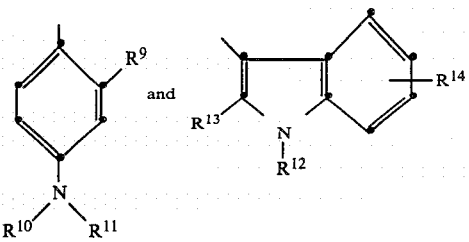

in which R$^3$ and R$^9$ independently represent hydrogen, non-tertiary C$_1$ to C$_4$ alkyl, non-tertiary C$_1$ to C$_4$ alkoxy, acylamino in which acyl is non-tertiary C$_2$ to C$_4$ alkyl or dialkylamino in which alkyl is non-tertiary C$_1$ to C$_4$ alkyl, R$^4$ and R$^{10}$ independently represent non-tertiary C$_1$ to C$_4$ alkyl, benzyl or benzyl substituted in the benzene ring by one or two of halo or C$_1$ to C$_3$ alkyl, R$^5$ and R$^{11}$ independently represent non-tertiary C$_1$ to C$_4$ alkyl, benzyl or benzyl substituted in the benzene ring by one or two or halo or C$_1$ to C$_3$ alkyl, R$^6$ and R$^{12}$ independently represent hydrogen, non-tertiary C$_1$ to C$_{16}$ alkyl, non-tertiary C$_2$ to C$_8$ alkylene, phenoxyethyl, benzyl or benzyl substituted in the benzene ring by one or two of halo or non-tertiary C$_1$ to C$_4$ alkyl, R$^7$ and R$^{13}$ independently represent hydrogen, C$_1$ to C$_3$ alkyl or phenyl, and R$^8$ and R$^{14}$ independently represent hydrogen, halo, non-tertiary C$_1$ to C$_4$ alkyl, non-tertiary C$_1$ to C$_4$ alkoxy or nitro.

Preferred articles within the fourth article of manufacture are those wherein the color-forming component comprises an isomeric mixture of 6-(N-R$^1$-amino)-7-[2-R$^3$-4-(N-R$^4$-N-R$^5$-amino)phenyl]-7-(1-R$^{12}$-2-R$^{13}$-5/6-R$^{14}$-indol-3-yl)-(5H)-pyrrolo-[3,4-b]-pyridin-5-ones of Formula XIX and 5-[2-R$^3$-4-(N-R$^4$-N-R$^5$-amino)-phenyl]-5-(1-R$^{12}$-2-R$^{13}$-5/6-R$^{14}$-indol-3-yl)-6-(N-R$^1$-amino)-(7H)-pyrrolo-[3,4-b]-pyridin-7-ones of Formula XX in which R$^1$, R$^3$, R$^4$, R$^5$, R$^{12}$, R$^{13}$ and R$^{14}$ each have the same respective meanings given in Formulas XVII and XVIII; and an isomeric mixture of 6-(N-R$^1$-amino)-7-(1-R$^6$-2-R$^7$-5/6-R$^8$-indol-3-yl)-7-(1-R$^{12}$-2-R$^{13}$-5/6-R$^{14}$-indol-3-yl)-(5H)-pyrrolo-[3,4-b]-pyridin-7-ones of Formula XX and 5-(1-R$^6$-2-R$^7$-5/6-R$^8$-indol-3-yl)-5-(1-R$^{12}$-2-R$^{13}$-5/6-R$^{14}$-indol-3-yl)-6-(N-R$^1$-amino)-(7H)-pyrrolo-[3,4-b]-pyridin-7-ones of Formula XXII in which R$^1$, R$^6$, R$^7$, R$^8$, R$^{12}$, R$^{13}$ and R$^{14}$ each have the same respective meanings given in Formulas XVII and XVIII.

In its first process aspect, the invention sought to be patented resides in the process for preparing a compound selected from the group having the structural formulas

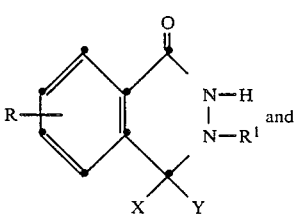

Formula I

-continued

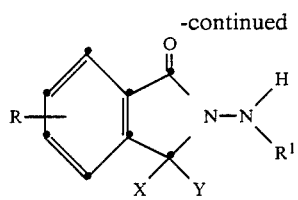

Formula XII and mixtures thereof wherein: R represents hydrogen, dialkylamino in which alkyl is non-tertiary $C_1$ to $C_4$ alkyl, $COOR^2$ in which $R^2$ is hydrogen or non-tertiary $C_1$ to $C_{16}$ alkyl or one to four halo; $R^1$ represents hydrogen, $C_1$ to $C_3$ alkyl, pyridyl,

in which Z is non-tertiary $C_1$ to $C_4$ alkoxy, $NHNH_2$ or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino; X is selected from the group consisting of

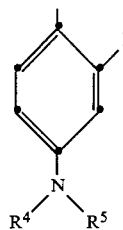 and 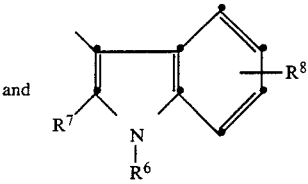

and Y is selected from the group consisting of hydrogen,

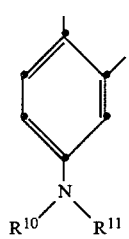 and 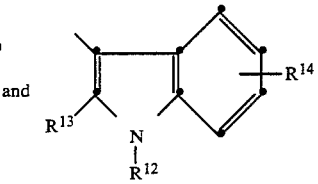

in which $R^3$ and $R^9$ independently represent hydrogen, non-tertiary $C_1$ to $C_4$ alkyl, non-tertiary $C_1$ to $C_4$ alkoxy, acylamino in which acyl is non-tertiary $C_1$ to $C_4$ alkyl or dialkylamino in which alkyl is non-tertiary $C_1$ to $C_4$ alkyl, $R^4$ and $R^{10}$ independently represent non-tertiary $C_1$ to $C_4$ alkyl, benzyl or benzyl substituted in the benzene ring by one or two of halo or $C_1$ to $C_3$ alkyl, $R^5$ and $R^{11}$ independently represent non-tertiary $C_1$ to $C_4$ alkyl, benzyl or benzyl substituted in the benzene ring by one or two or halo or $C_1$ to $C_3$ alkyl, $R^6$ and $R^{12}$ independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or non-tertiary $C_1$ to $C_4$ alkyl, $R^7$ and $R^{13}$ independently represent hydrogen, $C_1$ to $C_3$ alkyl or phenyl, and $R^8$ and $R^{14}$ independently represent hydrogen, halo, non-tertiary $C_1$ to $C_4$ alkyl, non-tertiary $C_1$ to $C_4$ alkoxy or nitro with the proviso that when $R^3$ and $R^9$ are both hydrogen, $R^4$, $R^5$, $R^{10}$ and $R^{11}$ can not simultaneously be non-tertiary $C_1$ to $C_4$ alkyl which comprises interacting a compound having the structural formula

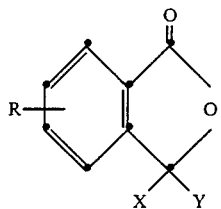

Formula XXIII with a compound of the structural formula $R^1NHNH_2$

Formula XXIV

In its second process aspect, the invention sought to be patented resides in the process for preparing a compound selected from the group having the structural formulas

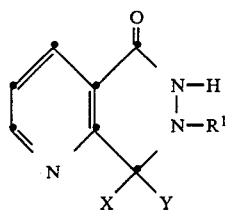

Formula VI

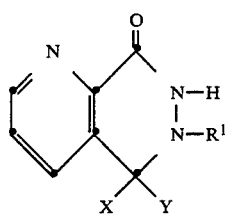

Formula VII

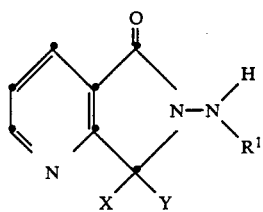

Formula XVII and

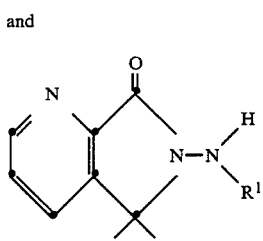

Formula XVIII and mixtures thereof wherein: $R^1$ is hydrogen, $C_1$ to $C_3$ alkyl, pyridyl,

in which Z is non-tertiary $C_1$ to $C_4$ alkoxy, $NHNH_2$ or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino; X is selected from the group consisting of

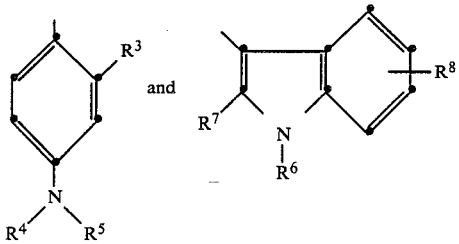

and Y is selected from the group consisting of hydrogen,

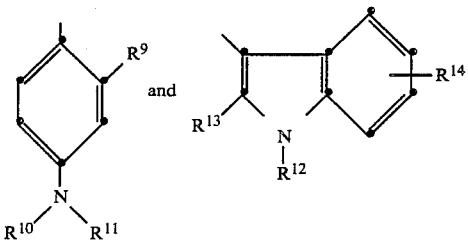

in which $R^3$ and $R^9$ independently represent hydrogen, non-tertiary $C_1$ to $C_4$ alkyl, non-tertiary $C_1$ to $C_4$ alkoxy, acylamino in which acyl is non-tertiary $C_2$ to $C_4$ alkyl or dialkylamino in which alkyl is non-tertiary $C_1$ to $C_4$ alkyl, $R^4$ and $R^{10}$ independently represent non-tertiary $C_1$ to $C_4$ alkyl, benzyl or benzyl substituted in the benzene ring by one or two of halo or $C_1$ to $C_3$ alkyl, $R^5$ and $R^{11}$ independently represent non-tertiary $C_1$ to $C_4$ alkyl, benzyl or benzyl substituted in the benzene ring by one or two or halo or $C_1$ to $C_3$ alkyl, $R^6$ and $R^{12}$ independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or non-tertiary $C_1$ to $C_4$ alkyl, $R^7$ and $R^{13}$ independently represent hydrogen, $C_1$ to $C_3$ alkyl or phenyl, and $R^8$ and $R^{14}$ independently represent hydrogen, halo, non-tertiary $C_1$ to $C_4$ alkyl, non-tertiary $C_1$ to $C_4$ alkoxy or nitro which comprises interacting an isomeric mixture having the structural formulas

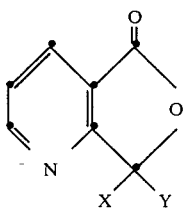

Formula XXV and

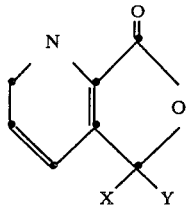

Formula XXVI with a compound having the structural formula $R^1NHNH_2$

Formula XXIV

As used herein the term "halo" includes chloro, fluoro, bromo and iodo. Chloro is the preferred halo substituent because of the relatively low cost and ease of preparation of the required chloro-substituted intermediates and because the other halogens offer no particular advantages over chloro. However, the other above-named halo substituents are also satisfactory.

The term "dialkylamino in which alkyl is non-tertiary $C_1$ to $C_4$ alkyl" denotes saturated, acyclic groups which may be straight or branched as exemplified by dimethylamino, diethylamino, ethylmethylamino, dipropylamino, dibutylamino, isobutylmethyl and the like.

As used herein the terms "$C_1$ to $C_3$ alkyl", "non-tertiary $C_1$ to $C_4$ alkyl", and "non-tertiary $C_1$ to $C_{16}$ alkyl" denote saturated monovalent straight or branched aliphatic hydrocarbon radicals including methyl, ethyl, propyl, isopropyl, butyl, isobutyl, amyl, 1-methylbutyl, 3-methylbutyl, hexyl, isohexyl, heptyl, isoheptyl, octyl, isooctyl, 2-ethylhexyl, nonyl, 3-ethylheptyl, decyl, undecyl, dodecyl, tridecyl, 1,3,5-trimethylhexyl, 1,5-dimethyl-4-ethylhexyl, 5-methyl-2-butylhexyl, 2-propylnonyl, 2-butyloctyl, 2-pentanonyl, and the like.

The term "non-tertiary $C_1$ to $C_4$ alkoxy" includes saturated acyclic, straight or branched-chained groups as methoxy, ethoxy, propoxy, isopropoxy, butoxy, sec-butoxy, and isobutoxy.

As used herein, the term "$C_2$ to $C_8$ alkenyl" means monovalent aliphatic radicals possessing a single double bond, for example, ethenyl (or vinyl), 2-propenyl (or allyl), 1-methylethenyl or (isopropenyl), 2-methyl-2-propenyl, 2-methyl-1-propenyl, 2-butenyl, 3-butenyl, 1-pentenyl, 2-pentenyl, 3-methyl-2-butenyl, 2-methyl-1-butenyl (isoamylenyl), 3-methyl-1-butenyl, 1-hexenyl, 2-hexenyl, 3-hexenyl, 2-heptenyl and 1-octenyl.

The compounds of Formulas I, VI, VII, XII, XVII and XVIII hereinabove are essentially colorless in the depicted form. When contacted with an electric current from an applied voltage stylus of the type ordinarily employed in electrochromic recording systems, the compounds of Formulas I, VI, VII, XII, XVII and XVIII develop yellow, yellow-brown, yellow-green, blue-green, blue, purple, magenta, and gray-colored images. These developed images are very insensitive to light, that is, once the color is developed it remains unchanged when subjected to light exposure. The developed images also possess excellent xerographic copiability.

The compounds of this invention may be incorporated in any of the commercially-accepted systems known in the electrochromic recording art. Typical techniques for the application of the color formers to paper are well-known and are described in numerous patents, for example, U.S. Pat. Nos. Re. 29,427; 3,726,769; 3,864,684; 3,871,972; 3,951,757; 4,017,366; and 4,133,933. The usual paper coatings consist of the color-forming component, an organic metal salt, a binder and some type of conductor, either an inorganic salt or a conductive polymer. This mixture is milled together optionally in the presence of a non-ionic surface active agent until the desired particle size is obtained and then the mixture is coated on paper and dried. Optionally, the color-forming substance can be milled in the presence of a binder and the remaining components milled also in the presence of a binder and the two mixtures combined together prior to coating on paper. Normally the surface of the coated paper is wet with a conductive solution containing an inorganic alkaline metal or alkaline earth metal salt, for example, potassium chloride, calcium chloride, sodium chloride, sodium bromide, potassium bromide, potassium nitrate or sodium sulfate immediately prior to the printing with the applied voltage stylus. For a quick qualitative test, it has been determined that the color-forming component can be dissolved in a suitable volatile organic solvent, coated on paper and the coated paper dried to obtain a paper sheet coated with the color-forming component. This coated sheet can then be wet with a conductive salt solution and an image traced with an applied voltage stylus to develop the colored image.

The compounds of Formulas I, VI, VII, XII, XVII and XVIII can be used alone as color-forming components in electrochromic recording paper or can be used in admixture with one or more other color-forming groups of compounds from the classes consisting of phthalides, for example, Crystal Violet Lactone; fluorans, for example, 3-diethylamino-5,7-dimethylfluoran; redox indicators, for example, phenothiazines such as benzoyl leuco methylene blue and various other types of color-forming components currently employed in commercially-accepted electrochromic recording systems.

The best mode contemplated by the inventors of carrying out this invention will now be described so as to enable any person skilled in the art to which it pertains to make and use the same.

In accordance with the aforementioned process aspects of this invention, the compounds of Formulas I, VI, VII, XII, XVII and XVIII are obtained by reacting lactone compounds of Formulas XXIII, XXV and XXVI with a $R^1$ substituted hydrazine of Formula XXIV. This reaction is conveniently carried out in an appropriate inert organic liquid, for example, a lower alkyl alcohol such as ethanol or propanol; a glycol such as ethylene glycol or propylene glycol; or a glycol ether such as ethoxyethanol commonly known as the ethyl ether of ethylene glycol. Alternatively, the reaction can be run neat with excess hydrazine, for example, phenylhydrazine serving as the reaction medium. This reaction is conveniently carried out at a temperature in the range of 90° to 198° C., usually at the reflux temperature for periods of approximately thirty minutes to approximately eighteen days. The compounds of Formulas I, VI, XII, XVII and XVIII thus obtained are isolated directly from the reaction medium after chilling. Alternatively, the desired product can be isolated by pouring the reaction mixture into a mixture of ice and water and filtering the resulting product. The isolated product can be purified by conventional means such as recrystallization or reslurrying with a suitable organic liquid followed by filtration. Alternatively, the purification can be combined with the isolation by extracting the mixture of ice, water and product with a suitable water immiscible organic liquid, for example, toluene and then concentrating the organic liquid solution of the product by conventional means such as evaporation or distillation. In some instances, the compounds of Formulas I, VI and VII are insoluble in the reaction medium and are removed by filtration. The filtrate is then poured into a mixture of ice and water and the compounds of Formulas XII, XVII and XVIII are isolated by filtration.

It will, of course, be appreciated that some of the starting phthalides and furopyridinones are isomers and mixtures of isomers by virtue of their method of preparation as described in some of the patents indicated hereinbelow. Throughout this application the nomenclature 5/6- is adopted in reference to 5/6-carboxyphthalides and esters thereof used as starting materials to produce 6/7-carboxy-phthalazinones and esters thereof and 5/6-carboxyphthalimidines and esters thereof. Further, it will be appreciated that the reaction of an inherently unsymmetrical anhydride in the preparation of the furopyridinones can produce isomers and mixtures of isomers. Since both isomers are useful in the practice of this invention, the mixture of isomers formed was utilized as the starting lactones in the practice of this invention.

The lactones of Formula XXIII, XXV and XXVI hereinabove, which are required as starting materials in the preparation of the final products of Formulas I, VI, VII, XII, XVII and XVIII are generally known generically as phthalides and furopyridinones. The following are examples illustrative of a few of these lactones which can be utilized in this invention: diaryl phthalides, for example, 3,3-bis(4-dimethylaminophenyl)-6-dimethylaminophthalide commonly known as crystal violet lactone, or simply CVL, 3-(4-dimethylaminophenyl)-3-[2,4-bis(dimethylamino)phenyl]-6-dimethylaminophthalide and similar compounds described in U.S. Pat. No. 4,094,877 which issued June 13, 1978; aryl heteryl phthalides, for example, 3-[2,4-bis(dimethylamino)phenyl]-3-(1-ethyl-2-methyl-3-indolyl)phthalide disclosed in Belgian Pat. No. 864,376, granted Aug. 28, 1978, and similar compounds found in U.S. Pat. Nos. 3,491,112 and 4,153,609 which issued Jan. 20, 1970 and May 8, 1979, respectively; bis(heteryl)phthalides, for example, 3,3-bis(1-ethyl-2-methyl-3-indolyl)phthalide, 3,3-bis(1-n-butyl-2-methyl-3-indolyl)phthalide and similar compounds described in U.S. Pat. Nos. 3,509,173 and 4,102,893 which issued Jan. 20, 1970 and July 5, 1978, respectively; 3-(2-ethoxy-4-diethylaminophenyl)-3-(1,2-dimethylindol-3-yl)-5/6-ethoxycarbonylphthalide and similar compounds described in U.S. Pat. No. 4,189,171 which issued Feb. 19, 1980; and furopyridinones, for example, 5/7-(2-methoxy-4-diethylaminophenyl)-5/7-(1-ethyl-2-methyl-3-indolyl)-furo[3,4b]-pyridine-5(7H)/7(5H)-one, described in Japanese Patent Publication 118,515/74, which published Nov. 13, 1974.

The hydrazines and hydrazides of Formula XXIV constitute an old and well-known class of compounds many of which are commercially-available or are readily obtained by conventional syntheses well-known in the art. The following list exemplifies hydrazines useful in carrying out the process of this invention. Hydrazine, 2-aminophenylhydrazine, benzylhydrazine, 2-bromophenylhydrazine, 3-bromophenylhydrazine, 4-bromophenylhydrazine, 2-chlorophenylhydrazine, 3-chlorophenylhydrazine, 4-chlorophenylhydrazine, 2,4-dichlorophenylhydrazine, 2,5-dichlorophenylhydrazine, 2,6-dichlorophenylhydrazine, 3,4-dichlorophenylhydrazine, 3,5-dichlorophenylhydrazine, 2,4-dinitrophenylhydrazine, 4-methoxyphenylhydrazine, methylhydrazine, 2-nitrophenylhydrazine, 3-nitrophenylhydrazine, 4-nitrophenylhydrazine, phenylhydrazine, 2-methylphenylhydrazine, 3-methylphenylhydrazine, 4-methylphenylhydrazine, methylhydrazinocarboxylate, acethydrazide, carbohydrazide, and pyridylhydrazine.

The molecular structures of the compounds of this invention were assigned on the basis of the modes of synthesis and study of their infrared and nuclear magnetic resonance spectra.

The following examples will further illustrate the invention without, however, limiting it thereto. All melting points are uncorrected.

EXAMPLE 1

With stirring, a mixture of 1200.0 ml of 80 percent aqueous ethyl alcohol, 25.0 g of 3,3-bis(4-dimethylaminophenyl)-6-dimethylaminophthalide and 35.4 g of 85 percent hydrazine hydrate was maintained at reflux temperature, approximately 90° C., for approximately three hours. After setting overnight at ambient temperature, the resulting slurry was chilled to approximately 5° C. by means of an external ice bath. The solid was collected by filtration, washed four times each with 50.0 ml of cold water and air-dried to obtain 20.8 g of 4,4-bis(4-dimethylaminophenyl)-7-dimethylaminophthalazin-1(2H)-one (Formula III: $R=N(CH_3)_2$; $R^1=R^3=R^9=H$; $R^4=R^5=R^{10}=R^{11}=CH_3$), a white-colored solid which melted at 265°–270° C. Significant infrared maxima appeared at 1660 cm$^{-1}$ (C=O;s) and 3400 cm$^{-1}$ (N-H;m). The nuclear magnetic resonance spectrum was consistent with the assigned structure. Paper treated with an ink formulation of the product produced a blue-green-colored image when traced with an applied voltage stylus.

EXAMPLE 2

A mixture of 25.0 g of 3,3-bis(4-dimethylaminophenyl)-6-dimethylaminophthalide, 300.0 ml of ethylene glycol and 35.4 g of 85 percent hydrazine hydrate was maintained at reflux temperature for approximately three days. The resultant mixture was cooled to room temperature. The solid was collected by filtration, washed with chilled ethyl alcohol and dried in vacuo to obtain 8.4 g of a mixture of 4,4-bis(4-dimethylaminophenyl)-7-dimethylaminophthalazin-1(2H)-one (Formula III: $R=N(CH_3)_2$; $R^1=R^3=R^9=H$; $R^4=R^5=R^{10}=R^{11}=CH_3$) and 2-amino-3,3-bis(4-dimethylaminophenyl)-6-dimethylaminophthalimidine (Formula XIV: $R=N(CH_3)_2$; $R^1=R^3=R^9=H$; $R^4=R^5=R^{10}=R^{11}=CH_3$). The filtrate was added slowly with stirring to a mixture of ice and water. The solid which separated was collected by filtration, washed with chilled water and dried to obtain 10.1 g of 2-amino-3,3-bis(4-dimethylaminophenyl)-6-dimethylaminophthalimidine (Formula XIV: $R=N(CH_3)_2$; $R^1=R^3=R^9=H$; $R^4=R^5=R^{10}=R^{11}=CH_3$), a green-colored solid which melted at 133°–135° C. Significant infrared maxima appeared at 3400 cm$^{-1}$ (N-H;m) and 1685 cm$^{-1}$ (C=O;s). The nuclear magnetic resonance spectrum was in accord with the assigned structure. Paper treated with an ink formulation of the product produced a blue-colored image when traced with an applied voltage stylus.

EXAMPLE 3

A mixture of 25.0 g of 3-(4-dimethylaminophenyl)-6-dimethylaminophthalide, 1700.0 ml of 40 percent aqueous ethyl alcohol and 49.5 g of 85 percent hydrazine hydrate was maintained at reflux temperature with stirring for approximately twenty-four hours. The reaction mixture was cooled to ambient temperature and slowly poured into a mixture of ice and water with stirring. The resulting solid was collected by filtration, washed with water and dried to obtain 19.83 g of a mixture of 4-(4-dimethylaminophenyl)-7-dimethylaminophthalazin-1(2H)-one (Formula II: $R=N(CH_3)_2$; $R^1=R^3=Y=H$; $R^4=R^5=CH_3$) and 2-amino-3-(4-dimethylaminophenyl)-7-dimethylamminophthalimidine (Formula XIII: $R=N(CH_3)_2$; $R^1=R^3=Y=H$; $R^4=R^5=CH_3$), a solid which melted over the range of 181.7°–189.4° C. The solid was suspended in warm ethyl alcohol and stirred for approximately one-half hour. The solid was collected by filtration, washed with a small amount of ethyl alcohol and dried to obtain 2.0 g of 4-(4-dimethylaminophenyl)-7-dimethylaminophthalazin-1(2H)-one, a pale gray-colored solid which melted at 230°–233° C. Infrared maxima appeared at 3215 cm$^{-1}$ (N-H;m) and 1667 cm$^{-1}$ (C=O;s). The nuclear magnetic resonance spectrum was in accord with the assigned structure. Paper treated with an ink formulation of the product produced a gray-colored image when trace with an applied voltaage stylus. The ethyl alcohol filtrate was poured slowly into water with stirring. The solid which precipitated was collected by filtration, washed with water and dried to obtain 16.0 g of 2-amino-3-(4-dimethylaminophenyl)-6-dimethylaminophthalimidine, a pale tan-colored solid which melted at 180°–181° C. Significant infrared maxima appeared at 3440 cm$^{-1}$ (N-H;m) and 1685 cm$^{-1}$ (C=O;s). The nuclear magnetic resonance spectrum was in accord with the assigned structure. Paper treated with an ink formulation of the product produced a blue-colored image.

EXAMPLE 4

A. With stirring, a mixture of 25.0 g of 3,3-bis(1-butyl-2-methylindol-3-yl)phthalide, 300.0 ml of ethylene glycol and 29.4 g of 85 percent hydrazine hydrate was maintained at reflux temperature approximately two days. After cooling to ambient temperature, the resulting slurry was added slowly with stirring into a mixture of ice and water. The solid was collected by filtration, washed with water and dried in vacuo to obtain 21.7 g of 2-amino-3,3-bis(1-butyl-2-methylindol-3-yl)phthalimidine (Formula XVI: $R=R^1=R^8=R^{14}=H$; $R^6=R^{12}=C_4H_9$; $R^7=R^{13}=CH_3$), a yellow solid which melted at 103°–105° C. Infrared maxima appeared at 3440 cm$^{-1}$ (N-H;s), 1690 cm$^{-1}$ (C=O;s) and 750 cm$^{-1}$ (indole;s). The nuclear magnetic resonance spectrum was consistent with the assigned structure.

B. Four and one-half grams of the product from part A above was dissolved in 150.0 ml of hot ethyl alcohol and the resulting solution was stirred for approximately thirty minutes with 1.0 g of decolorizing charcoal. The carbon was removed by filtration and the filtrate was concentrated to approximately fifty milliliters by evaporation. To the resultant concentrate 200.0 ml of cyclohexane was added and the mixture was cooled slowly.

The solid which formed was collected by filtration and dried to obtain 3.4 g of 2-amino-3,3-bis(1-butyl-2-methylindol-3-yl)phthalimidine, a white solid which melted at 153°–154° C. Paper treated with an ink formulation of the product produced a purple-colored image when traced with an applied voltage stylus.

EXAMPLE 5

With stirring, a mixture of 25.0 g of 3,3-bis(1-butyl-2-methylindol-3-yl)phthalide, 800.0 ml of ethyl alcohol, 200.0 ml of water and 29.4 g of 85 percent hydrazine hydrate was maintained at reflux temperature for approximately forty-eight hours. The resulting mixture was chilled in an external ice bath to a temperature in the range of 0°–5° C. The solid was collected by filtration, washed with chilled ethyl alcohol and dried in an air oven to obtain 23.65 g of 4,4-bis(1-butyl-2-methylindol-3-yl)-phthalazin-1(2H)-one (Formula V: $R=R^1=R^8=R^{14}=H$; $R^6=R^{12}=C_4H_9$; $R^7=R^{13}=CH_3$), a pale orange-colored solid which melted at 205.5°–206.5° C. In the infrared spectrum maxima appeared at 3400 cm$^{-1}$ (N-H;w) and 1670 cm$^{-1}$ (C=O;s). The nuclear magnetic resonance spectrum was consistent with the assigned structure. Paper treated with an ink formulation of the product produced a purple-colored image when traced with an applied voltage stylus.

EXAMPLE 6

A. A mixture of 10.0 g of 3,3-bis(4-dimethylaminophenyl)-6-dimethylaminophthalide and 26.0 g of phenylhydrazine was maintained at a temperature in the range of 140°–150° C. with stirring for approximately thirty hours. The solid was collected by filtration, washed with toluene and air-dried to obtain 8.7 g of a yellow solid. The solid was slurried in warm ethyl alcohol for approximately one hour. The solid was collected by filtration and washed with a small portion of ethyl alcohol. The alcohol filtrate was added slowly to water with stirring. The solid which formed was collected by filtration, washed with water and dried to obtain 4.2 g of 2-anilino-3,3-bis(4-dimethylaminophenyl)-6-dimethylaminophthalimidine (Formula III: $R=N(CH_3)_2$; $R^1=C_6H_5$; $R^3=R^9=H$; $R^4=R^5=R^{10}=R^{11}=CH_3$), a bright yellow solid which melted at 143°–145° C. Significant infrared maxima appeared at 3420 cm$^{-1}$ (N-H;w) and 1700 cm$^{-1}$ (C=O;s). The nuclear magnetic resonance spectrum was in accord with the assigned structure.

B. A mixture of 3.0 g of the product from A above and 30.0 ml of ethyl alcohol was maintained at reflux temperature for approximately fifteen minutes. The solid was collected by filtering the hot mixture and was washed first with 20.0 ml of hot ethyl alcohol and then with 20.0 ml of room temperature alcohol and dried to obtain 2.1 g of 2-anilino-3,3-bis(4-dimethylaminophenyl)-6-dimethylaminophthalimidine, a yellow solid which melted over the range of 217°–222° C. Paper treated with an ink formulation containing the product produced a blue-colored image when traced with an applied voltage stylus.

EXAMPLE 7

With stirring a mixture of 10.0 g of 3-(1-butyl-2-methylindol-3-yl)-3-(1-tetradecyl-2-methylindol-3-yl)phthalide, 9.4 g of 85 percent hydrazine hydrate and 50.0 ml of 2-ethoxyethanol was maintained at approximately 100° C. for approximately two hours. After cooling the reaction mixture to approximately 50° C., there was added slowly 75.0 ml of 5 percent aqueous ammonium hydroxide and 75.0 ml of toluene and a small portion of saturated sodium chloride solution. The water layer was separated and extracted a second time with 75.0 ml of fresh toluene. The two toluene portions were combined, washed with saturated sodium chloride solution, and dried over anhydrous sodium sulfate. The dried toluene layer was then concentrated under vacuum to obtain 11.5 g of 4-(1-butyl-2-methylindol-3-yl)-4-(1-tetradecyl-2-methylindol-3-yl)phthalazin-1(2H)-one (Formula V: $R=R^1=R^8=R^{14}=H$; $R^6=C_4H_9$; $R^7=R^{13}=CH_3$; $R^{12}=C_{14}H_{29}$), a thick dark brown oil which upon standing turned into a wax-like solid. A significant infrared maximum appeared at 1668 cm$^{-1}$ (C=O;s). The nuclear magnetic resonance spectrum was consistent with the assigned structure. Paper treated with an ink formulation of the product produced a magenta-colored image when traced with an applied voltage stylus.

EXAMPLE 8

With stirring a mixture of 16.6 g of 3,3-bis(4-dimethylaminophenyl)-6-(4-dimethylamino)phthalide and 9.0 g of methylhydrazinocarboxylate was maintained at 100°–110° C. for approximately one hour and then maintained at approximately 150° C. for approximately eighteen hours. The reaction mixture was maintained at 175° C. for approximately one hour and at approximately 205° C. for approximately twenty-one hours. The reaction mass was broken-up, added to water and stirred at ambient temperature for approximately four hours. After sitting overnight, the slurry was stirred an additional two hours and the solid was collected by filtration. The solid was dried in vacuo obtaining 11.4 g of 2-(methoxycarbonylamino)-3,3-bis(4-dimethylaminophenyl)-6-dimethylaminophthalimidine (Formula XIV: $R=N(CH_3)_2$; $R^1=CO_2CH_3$; $R^3=R^9=H$; $R^4=R^5=R^{10}=R^{11}=CH_3$), a brown-colored solid which melted at 98° C. with decomposition. A significant infrared maximum appeared at 1665 cm$^{-1}$ (C=O;s). The nuclear magnetic resonance spectrum was in accord with the assigned structure. Paper treated with an ink formulation of the product produced a blue-green-colored image when traced with an applied voltage stylus.

EXAMPLE 9

Following the procedure described in Example 8 above, a mixture of 12.5 g of 3,3-bis(4-dimethylaminophenyl)-6-dimethylaminophthalide and 14.8 g of acethydrazide was maintained at approximately 140° C. for approximately two and one-half hours, then at 160° C. for approximately eighteen hours and finally at approximately 180° C. for approximately ninety minutes to obtain, after slurrying the reaction mass in water and drying, 9.7 g of 2-(acetylamino)-3,3-bis(4-dimethylaminophenyl)-6-dimethylaminophthalimidine (Formula XIV: $R=N(CH_3)_2$; $R^1=COCH_3$; $R^3=R^9=H$; $R^4=R^5=R^{10}=R^{11}=CH_3$), a pale white-colored solid which melted over the range 205°–215° C. A significant infrared maximum appeared at 1665 cm$^{-1}$ (C=O;m). The nuclear magnetic resonance spectrum was concordant with the assigned structure. Paper treated with an ink formulation of the product produced a blue-colored image when traced with an applied voltage stylus.

EXAMPLE 10

Proceeding in a manner similar to that described in Example 8 above, a mixture of 12.5 g of 3,3-bis(4-dimethylaminophenyl)-6-dimethylaminophthalide and 9.0 g of carbohydrazide was maintained at approximately 180° C. for approximately thirty-five hours to obtain, after reslurrying in water and drying, 9.8 g of 2-(hydrazinocarbonylamino)-3,3-bis(4-dimethylaminophenyl)-6-dimethylaminophthalimidine (Formula XIV: $R=N(CH_3)_2$; $R^1=CONHNH_2$; $R^3=R^9=H$; $R^4=R^5=R^{10}=R^{11}=CH_3$), a brown-colored solid which melted at 221°–225° C. A significant infrared maximum appeared at 1610 cm$^{-1}$ (C=O;s). The nuclear magnetic resonance spectrum was in accord with the assigned structure. Paper treated with an ink formulation of the product produced a blue-colored image when traced with an applied voltage stylus.

Proceeding in a manner similar to that described in Example 3 above, the appropriate substituted phthalide or furopyridinone described in Column 2 hereinbelow was interacted with hydrazine hydrate or other substituted hydrazine in the organic medium given in Column 4 below at the temperature of the mixture given in Column 5 for the period of time indicated in Column 6 below. The product that was obtained is given in Column 7 having the formula indicated in Column 8 with its physical appearance in Column 9, its melting point in Column 10, significant infrared maxima are indicated in Column 11 and its nuclear magnetic resonance spectral analysis in Column 13 and the color produced when a paper sheet treated with an ink formulation containing the product was traced with an applied voltage stylus is given in Column 14.

TABLE A

| Example No. | Starting Phthalide | Hydrazine Hydrate | Organic Medium | Temperature | Reaction Time | Product | Product Formula | Physical Appearance | Melting Point | Significant Infrared | NMR | Produced Image Color |
|---|---|---|---|---|---|---|---|---|---|---|---|---|
| 11 | 20.0 g 3-(4-Dimethylaminophenyl)-3-(2-ethoxy-4-diethylaminophenyl)-6-dimethylaminophthalide | 24.1 g of 85 percent | 1114.0 ml of 40 percent ethyl alcohol | Reflux | 28 hours | 19.85 g 4-(4-Dimethylaminophenyl)-4-(2-ethoxy-4-diethylaminophenyl)-7-dimethylaminophthalazin-1(2H)—one | III: R=N(CH$_3$)$_2$; R$^1$=R$^9$=H; R$^3$=OC$_2$H$_5$; R$^4$=R$^5$=C$_2$H$_5$; R$^{10}$=R$^{11}$=CH$_3$ | White Powder | 222.5–224.5° C. | 3425 cm$^{-1}$ (N—H;m) 1670 cm$^{-1}$ (C=O;s) | Consistent | Blue |
| 12 | 15.0 g 3,3-Bis(4-dimethylaminophenyl)phthalide | 23.5 g of 85 percent | 800 ml of 80 percent ethyl alcohol | Reflux | 3 days | 11.7 g 4,4-Bis(4-methylaminophenyl)-phthalazin-1(2H)—one | III: R=R$^1$=R$^3$=R$^9$=H, R$^4$=R$^5$=R$^{10}$=R$^{11}$=CH$_3$ | Pale Green Crystals | 203–205.5° C. | 3390 cm$^{-1}$ (N—H;m) 1665 cm$^{-1}$ (C=O;s) | Consistent | Blue-green |
| 13 | 15.0 g 3-(4-Dimethylaminophenyl)-3-[2,4-bis(dimethylamino)phenyl]-phthalide | 21.2 g of 85 percent | 720 ml of 80 percent ethyl alcohol | Reflux | 5 days | 8.6 g 4-(4-Dimethylaminophenyl)-4-[2,4-bis(dimethylamino)phenyl]phthalazin-1(2H)—one | III: R=R$^1$=R$^9$=H; R$^3$=N(CH$_3$)$_2$; R$^5$=R$^{10}$=R$^{11}$=CH$_3$; R$^4$=CH$_3$ | Pale Tan Solid | 214° C. with decomposition | 3380 cm$^{-1}$ (N—H;m) 1665 cm$^{-1}$ (C=O;s) | Consistent | Yellow-brown |
| 16 | 20.0 g 3-(4-Dimethylaminophenyl)-3-(1-butyl-2-methylindol-3-yl)-6-dimethylaminophthalide | 27.0 g of 85 percent | 920 ml of 80 percent ethyl alcohol | Reflux | 48 hours | 7.7 g 4-(4-Dimethylaminophenyl)-4-[2,4-bis(dimethylamino)phenyl]-7-dimethylaminophthalazin-1(2H)—one | III: R=R$^3$=N(CH$_3$)$_2$; R$^1$=R$^9$=H; R$^4$=R$^5$=R$^{11}$=CH$_3$ | Tan Powder | 226–229° C. | 3410 cm$^{-1}$ (N—H;m) 1666 cm$^{-1}$ (C=O;s) | Consistent | Blue-green |
| 15 | 10.0 g 3,3-Bis(2-methyl-4-diethylaminophenyl)phthalide | 12.9 g of 85 percent | 440.0 ml of 80 percent ethyl alcohol | Reflux | 18 days | 1.6 g 4,4-Bis(2-methyl-4-diethylaminophenyl)phthalazin-1(2H)—one | III: R=R$^1$=H, R$^3$=R$^9$=CH$_3$; R$^4$=R$^5$=R$^{10}$=R$^{11}$=C$_2$H$_5$ | Pale Blue-green Powder | 226.5–230° C. | 3400 cm$^{-1}$ (N—H;m) 1666 cm$^{-1}$ (C=O;s) | Consistent | Yellow |
| 14 | 25.0 g 3-(4-Dimethylaminophenyl)-3-[2,4-bis(dimethylamino)phenyl]-6-dimethylaminophthalide | 31.8 g of 85 percent | 1200.0 ml of 80 percent ethyl alcohol | Reflux | 96 hours | 16.4 g 4-(4-Dimethylaminophenyl)-4-(1-butyl-2-methylindol-3-yl)-7-dimethylaminophthalazin-1(2H)—one | IV: R=N(CH$_3$)$_2$; R$^1$=R$^3$=R$^{14}$=H; R$^4$=R$^5$=R$^{13}$=CH$_3$; R$^{12}$=C$_4$H$_9$ | Pale Green Powder | 153–161° C. | 3370 cm$^{-1}$ (N—H;m) 1663 cm$^{-1}$ (C=O;s) 750 cm$^{-1}$ (indole;s) | Consistent | Blue-green |
| 17 | 10.0 g 3-(2-Ethoxy-4-diethylaminophenyl)-3-(1-butyl-2-methylindol-3-yl)phthalide | 11.8 g of 85 percent | 400.0 ml of 80 percent ethyl alcohol | Reflux | 6 days | 8.6 g 4-(2-Ethoxy-4-diethylaminophenyl)-4-(1-butyl-2-methylindol-3-yl)phthalazin-1(2H)—one | IV: R=R$^1$=R$^{14}$=H; R$^3$=OC$_2$H$_5$; R$^4$=R$^6$=C$_2$H$_5$; R$^{12}$=C$_4$H$_9$; R$^{13}$=CH$_3$ | White Powder | 200–202° C. | 3300 cm$^{-1}$ (N—H;m) 1665 cm$^{-1}$ (C=O;s) 750 cm$^{-1}$ (indole;s) | Consistent | Yellow |
| 18 | 25.0 g 3-(2-Ethoxy-4-diethylaminophenyl)-3-(1-ethyl-2-methylindol-3-yl)-5/6-ethoxycarbonylphthalide | 30.6 g of 85 percent | 1040.0 ml of 80 percent ethyl alcohol | Reflux | 24 hours | 13.1 g 4-(2-Ethoxy-4-diethylaminophenyl)-4-(1-ethyl-2-methylindol-3-yl)-6/7-ethoxycarbonyl-phthalazin-1(2H)—one | IV: R=COOC$_2$H$_5$; R$^1$=R$^{14}$=H; R$^3$=OC$_2$H$_5$; R$^4$=R$^5$=R$^{12}$=C$_2$H$_5$; R$^{13}$=CH$_3$ | Pale Yellow Powder | 208–209° C. | 3400 cm$^{-1}$ (N—H;m) 1670 cm$^{-1}$ (C=O;s) | Consistent | phthalazin-1(2H)—one |
| 19 | 10.0 g 3-(1,2-Dimethylindol-3-yl)-3-(1-ethyl-2-methylindol-3-yl)-5/6-ethoxycarbonylphthalide | 11.2 g of 85 percent | 400.0 ml of 80 percent ethyl alcohol | Reflux | 9 days | 6.9 g 4-(1,2-Dimethylindol-3-yl)-4-(1-ethyl-2-methylindol-3-yl)-6/7-ethoxycarbonyl-phthalazin-1(2H)—one | V: R=COOC$_2$H$_5$; R$^1$=R$^8$=R$^{14}$=H; R$^6$=C$_2$H$_5$; R$^7$=R$^{12}$=R$^{13}$=CH$_3$ | Orange Powder | 103–105.5° C. | 3400 cm$^{-1}$ (N—H;m) 1670 cm$^{-1}$ (C=O;s) 750 cm$^{-1}$ | Consistent | Purple |

TABLE A-continued

| Example No. | Starting Phthalide | Hydrazine Hydrate | Organic Medium | Temperature | Reaction Time | Product | Product Formula | Physical Appearance | Melting Point | Significant Infrared | NMR | Produced Image Color |
|---|---|---|---|---|---|---|---|---|---|---|---|---|
| 20 | 5.1 g 3,3-Bis(1-ethyl-2-methyl-indol-3-yl)-5/6-methoxycarbonyl-phthalide | 5.0 ml of 85 percent | 60.0 ml of methyl alcohol 35.0 ml of ethyl alcohol | Reflux | 2½ hours | 1.3 g 4,4-Bis(1-ethyl-2-methylindol-3-yl)-6/7-methoxycarbonyl-phthalazin-1(2H)—one | V: R=COOCH$_3$; R$^1$=R$^8$=R$^{14}$=H; R$^6$=R$^{12}$=C$_2$H$_5$; R$^7$=R$^{13}$=CH$_3$ | White Solid | 227–230° C. | (indole;s) | Consistent | Magenta |
| 21 | 25.0 g 3-(1-Ethyl-2-methylindol-3-yl)-3-(1-butyl-2-methylindol-3-yl)phthalide | 30.6 g of 85 percent | 1040.0 ml of 80 percent ethyl alcohol | Reflux | 48 hours | 14.9 g 4-(1-ethyl-2-methylindol-3-yl)-4-(1-butyl-2-methylindol-3-yl)phthalazin-1(2H)—one | V: R=R$^1$=R$^8$=R$^{14}$=H; R$^6$=C$_2$H$_5$; R$^{12}$=C$_4$H$_9$; R$^7$=R$^{13}$=CH$_3$ | Pale Orange Powder | 186.5–193° C. | 3370 cm$^{-1}$ (N—H;m) 1665 cm$^{-1}$ (C=O;s) 750 cm$^{-1}$ (indole;s) | Consistent | Purple |
| 22 | 20.0 g Of an isomeric mixture of 7-[2-ethoxy-4-diethylaminophenyl]-7-(1-ethyl-2-methylindol-3-yl)-furo-[3,4b]-pyridine-5(7H)—one and 5-(2-ethoxy-4-diethylaminophenyl)-5-(1-ethyl-2-methylindol-3-yl)-furo-(3,4b)-pyridine-7(5H)—one | 24.7 g of 85 percent | 850.0 ml of 80 percent ethyl alcohol | Reflux | 6 days | 16.5 g Of an isomeric mixture of 8-(2-ethoxy-4-diethylaminophenyl)-8-(1-ethyl-2-methyl-indol-3-yl)-pyrido-[2,3d]-pyridazin-5(6H)—one and 5-(2-ethoxy-4-diethylaminophenyl)-5-(1-ethyl-2-methylindol-3-yl)-pyrido-[2,3d]-pyridazin-8(5H)—one | VIII & IX: R=R$^1$=R$^{14}$=H; R$^3$=OC$_2$H$_5$; R$^4$=R$^5$=R$^{12}$=C$_2$H$_5$; R$^{13}$=CH$_3$ | Pale Tan Powder | 215–219° C. | 3300 cm$^{-1}$ (N—H;m) 1670 cm$^{-1}$ (C=O;s) 750 cm$^{-1}$ (indole;s) | Consistent | Yellow-green |
| 23 | 25.0 g Of an isomeric mixture of 7-[2,4-bis(dimethylamino)phenyl]-7-(1-ethyl-2-methylindol-3-yl)-furo-[3,4b]-pyridine-5(7H)—one and 5-[2,4-bis(dimethylamino)phenyl]-5-(1-ethyl-2-methylindol-3-yl)-furo-[3,4b]-pyridine-7(5H)—one | 32.5 g of 85 percent | 1100.0 ml of 80 percent ethyl alcohol | Reflux | 6 days | 20.5 g Of an isomeric mixture of 8-[2,4-bis(dimethylamino)phenyl]-8-(1-ethyl-2-methyl-indol-3-yl)-pyrido-[2,3d]-pyridazine-5(6H)—one and 5-[2,4-bis(dimethylamino)phenyl]-5-(1-ethyl-2-methylindol-3-yl)-pyrido-[2,3d]-pyridazin-8(5H)—one | VIII & IX: R=R$^1$=R$^{14}$=H; R$^3$=N(CH$_3$)$_2$; R$^4$=R$^5$=R$^{13}$=CH$_3$; R$^{12}$=C$_2$H$_5$ | Pale Gray Powder | 242.5–246° C. | 3415 cm$^{-1}$ (N—H;m) 1669 cm$^{-1}$ (C=O;s) 752 cm$^{-1}$ (indole;s) | Consistent | Purple |

Following a procedure similar to that described in Example 7 above, the appropriate substituted phthalide described in Column 2 hereinbelow was interacted with the appropriate hydrazine given in Column 3 below in the organic medium given in Column 4 below at the temperature of the mixture given in Column 5 for the period of time indicated in Column 6 below. The product that was obtained is given in Column 7 having the formula indicated in Column 8 with its physical appearance described in Column 9, its melting point in Column 10, significant infrared maxima of the product is given in Column 11, its nuclear magnetic resonance spectral analysis indicated in Column 13 and the color produced when a paper sheet coated with an ink formulation containing the product was traced with an applied voltage stylus is given in Column 14.

TABLE B

| Example No. | Starting Phthalide | Hydrazine Hydrate | Organic Medium | Temperature | Reaction Time | Product | Product Formula | Physical Appearance | Melting Point | Significant Infrared | NMR | Produced Image Color |
|---|---|---|---|---|---|---|---|---|---|---|---|---|
| 24 | 10.0 g 3-(1-Octyl-2-methylindol-3-yl)-3-(1-phenoxyethyl-2-methyl-indol-3-yl)phthalide | 9.4 g of 85 percent | 100.0 ml 2-Ethoxyethanol | 100° C. | 6 hours | 7.5 g 4-(1-Octyl-2-methylindol-3-yl)-4-(1-phenoxyethyl-2-methylindol-3-yl)phthalazin-1(2H)—one | V; R=R$^1$=R$^8$=R$^{14}$=H; R$^6$=C$_8$H$_{17}$; R$^7$=R$^{13}$=CH$_3$; R$^{12}$=C$_6$H$_5$OC$_2$H$_4$ | White Powder | 172–174° C. | 1665 cm$^{-1}$ (C=O;s) | Consistent | Magenta |
| 25 | 5.0 g 3,3-Bis(1-phenoxyethyl-2-methylindol-3-yl)phthalide | 4.7 g of 85 percent | 50.0 ml 2-Ethoxyethanol | 100° C. | 20 hours | 1.0 g 4,4-Bis(1-phenoxyethyl-2-methylindol-3-yl)phthalazin-1(2H)—one | V; R=R$^1$=R$^8$=R$^{14}$=H; R$^6$=R$^{12}$=C$_6$H$_5$OC$_2$H$_4$; R$^7$=R$^{13}$=CH$_3$ | White Powder | 119–122° C. | 3420 cm$^{-1}$ (N—H;s) 1617 cm$^{-1}$ (C=O;s) | Consistent | Magenta |
| 26 | 25.0 g 3-(1-Butyl-2-methylindol-3-yl)-3-(1-ethyl-2-methylindol-3-yl)phthalide | 30.6 g of 85 percent | 300.0 ml Ethylene Glycol | 175° C. | 15 minutes | 21.8 g 2-Amino-3-(1-butyl-2-methylindol-3-yl)-3-(1-ethyl-2-methylindol-3-yl)phthalimidine | XVI; R=R$^1$=R$^8$=R$^{14}$=H; R$^6$=C$_8$H$_{17}$; R$^7$=R$^{13}$=CH$_3$; R$^{12}$=C$_2$H$_5$ | White Powder | 220–221° C. | 3440 cm$^{-1}$ (N—H;m) 1690 cm$^{-1}$ (C=O;s) | Consistent | Purple |
| 27 | 5.0 g 3-(1-Benzyl-2-methylindol-3-yl)-3-(1-ethyl-2-methylindol-3-yl)phthalide | 5.8 g of 85 percent | 75.0 ml 2-Ethoxyethanol | 100° C. | 15 hours | 2.4 g 4-(1-Benzyl-2-methylindol-3-yl)-4-(1-ethyl-2-methylindol-3-yl)phthalazin-1(2H)—one | V; R=R$^1$=R$^8$=R$^{14}$=H; R$^6$=C$_6$H$_5$CH$_2$; R$^7$=R$^{13}$=CH$_3$; R$^{12}$=C$_2$H$_5$ | Yellow Powder | 211–213° C. | 3400 cm$^{-1}$ (N—H;s) 1670 cm$^{-1}$ (C=O;s) | Consistent | Purple |
| 28 | 10.0 g 3-(1-Benzyl-2-methylindol-3-yl)-3-(1-octyl-2-methylindol-3-yl)phthalide | 10.0 g of 85 percent | 150.0 ml 2-Ethoxyethanol | 100° C. | 7 hours | 6.4 g 4-(1-Benzyl-2-methylindol-3-yl)-4-(1-octyl-2-methylindol-3-yl)phthalazin-1(2H)—one | V; R=R$^1$=R$^8$=R$^{14}$=H; R$^6$=C$_6$H$_5$CH$_2$; R$^7$=R$^{13}$=CH$_3$; R$^{12}$=C$_8$H$_{17}$ | Pale Orange Powder | 155–165° C. | 3420 cm$^{-1}$ (N—H;s) 1667 cm$^{-1}$ (C=O;s) | Consistent | Magenta |
| 29 | 5.0 g 3,3-Bis(4-dimethylaminophenyl)-6-dimethylaminophthalide | 13.1 g of 2-Hydrazino-pyridine | (none) | 155° C. | 24 hours | 2.2 g 2-(2-Pyridyl-amino)-3,3-bis(4-dimethylaminophenyl)-6-dimethylaminophthalimidine | XIV; R=N(CH$_3$)$_2$; R$^1$=2-pyridyl-amino; R$^3$=R$^9$=H; R$^4$=R$^5$=R$^{10}$=R$^{11}$=CH$_3$ | Tan Powder | 198–202° C. | 3440 cm$^{-1}$ (N—H;s) 1710 cm$^{-1}$ (C=O;s) | Consistent | Blue |
| 30 | 3.0 g 3-(1-Benzyl-2-methylindol-3-yl)-3-(1-octyl-2-methylindol-3-yl)-4,5,6,7-tetrachlorophthalide | 2.0 ml of 85 percent | 20.0 ml N,N-dimethyl-formamide | 40° C. | 18 hours | 2.1 g A mixture of 4-(1-Benzyl-2-methylindol-3-yl)-4-(1-octyl-2-methylindol-3-yl)-5,6,7,8-tetrachlorophthalazin-1(2H)—one and 2-amino-3-(1-benzyl-2-methylindol-3-yl)-3-(1-octyl-2-methylindol-3-yl)-4,5,6,7-tetrachlorophthalimidine | V & XVI; R=(Cl)$_4$; R$^1$=R$^8$=R$^{14}$=H; R$^6$=C$_6$H$_5$CH$_2$; R$^7$=R$^{13}$=CH$_3$; R$^{12}$=C$_8$H$_{17}$ | Pale Brown Powder | 110–113.5° C. | 3400 cm$^{-1}$ (N—H;s) 1740 cm$^{-1}$ (C=O;s) | Consistent | Purple |

Following a procedure similar to that described in Example 4 above, the appropriate substituted phthalide or furopyridinone described in Column 2 hereinbelow was interacted with hydrazine hydrate in the organic medium given in Column 4 below at the temperature of the mixture given in Column 5 for the period of time indicated in Column 6 below. The product that was obtained is given in Column 7 having the formula indicated in Column 8 with its physical appearance described in Column 9, its melting point in Column 10, significant infrared maxima of the product is given in Column 11, its nuclear magnetic resonance spectral analysis indicated in Column 13 and the color produced when a paper sheet coated with an ink formulation containing the product was traced with an applied voltage stylus is given in Column 14.

TABLE C

| Example No. | Starting Phthalide | Hydrazine Hydrate | Organic Medium | Temperature | Reaction Time | Product | Product Formula | Physical Appearance | Melting Point | Significant Infrared | NMR | Produced Image Color |
|---|---|---|---|---|---|---|---|---|---|---|---|---|
| 31 | 10.0 g 3-(4-Dimethylaminophenyl)-3-(1-ethyl-2-methylindol-3-yl)-6-dimethylaminophthalide | 12.9 g of 85 percent | 150.0 ml 2-Ethoxyethanol | 105° C. | 2 hours | 10.1 g 4-(4-Dimethylaminophenyl)-4-(1-ethyl-2-methylindol-3-yl)-7-dimethylaminophthalazin-1(2H)—one | IV: R=N(CH$_3$)$_2$; R$^1$=R$^3$=R$^{14}$=H; R$^4$=R$^5$=R$^{13}$=CH$_3$; R$^{12}$=C$_2$H$_5$ | Tan Solid | 208–212° C. | 3400 cm$^{-1}$ (N—H;m) 1660 cm$^{-1}$ (C=O;s) 750 cm$^{-1}$ (indole;s) | Consistent | Blue-green |
| 32 | 20.0 g 3-(2-Ethoxy-4-diethylaminophenyl)-3-(1-ethyl-2-methylindol-3-yl)phthalide | 24.1 g of 85 percent | 200.0 ml 2-Ethoxyethanol | Reflux | 2 hours | 18.7 g 4-(2-Ethoxy-4-diethylaminophenyl)-4-(1-ethyl-2-methylindol-3-yl)phthalazin-1(2H)—one | IV: R=R$^1$=R$^{14}$=H; R$^3$=OC$_2$H$_5$; R$^4$=R$^5$=R$^{12}$=C$_2$H$_5$; R$^{13}$=CH$_3$ | White Powder | 223.5–225° C. | 3420 cm$^{-1}$ (N—H;m) 1665 cm$^{-1}$ (C=O;s) 750 cm$^{-1}$ (indole;s) | Consistent | Gray |
| 33 | 25.0 g 3-(2-Ethoxy-4-diethylaminophenyl)-3-(1-ethyl-2-methylindol-3-yl)-5/6-carboxyphthalide | 27.6 g of 85 percent | 300.0 ml 2-Ethoxyethanol | 100° C. | 1 hour | 3.7 g 4-(2-Ethoxy-4-diethylaminophenyl)-4-(1-ethyl-2-methylindol-3-yl)phthalazin-1(2H)—one | IV: R=R$^1$=R$^{14}$=H; R$^3$=OC$_2$H$_5$; R$^4$=R$^5$=R$^{12}$=C$_2$H$_5$; R$^{13}$=CH$_3$ | Pale Tan Solid | 172–175° C. | 3350 cm$^{-1}$ (N—H;m) 1670 cm$^{-1}$ (C=O;s) 750 cm$^{-1}$ (indole;s) | Consistent | Yellow-brown |
| 34 | 25.0 g 3,3-Bis(1-ethyl-2-methylindol-3-yl)phthalide | 32.9 g of 85 percent | Ethylene glycol | Reflux | 30 minutes | 23.4 g 3,3-Bis(1-ethyl-2-methylindol-3-yl)phthalimidine | XVI: R$^8$=R$^{14}$=H; R$^6$=R$^{12}$=C$_2$H$_5$; R$^7$=R$^{13}$=CH$_3$ | White Powder | 143.5–145° C. | 3430 cm$^{-1}$ (N—H;m) 1690 cm$^{-1}$ (C=O;s) 750 cm$^{-1}$ (indole;s) | Consistent | Magenta |
| 35 | 5.0 g Of an isomeric mixture of 7,7-bis(1-ethyl-2-methylindol-3-yl)-furo-[3,4b]-pyridine-5[7H]—one and 5,5-bis(1-ethyl-2-methylindol-3-yl)-furo-[3,4b]-pyridine-7[5H]—one | 6.5 g of 85 percent | 50.0 ml 2-Ethoxyethanol | 100° C. | 6 hours | 4.3 g Of an isomeric mixture of 8,8-bis(1-ethyl-2-methylindol-3-yl)-pyrido-[2,3d]-pyridazin-5(6H)—one and 5,5-bis(1-ethyl-2-methylindol-3-yl)-pyrido-[2,3d]-pyridazin-8(5H)—one | X & XI: R=R$^1$=R$^8$=R$^{14}$=H; R$^6$=R$^{12}$=C$_2$H$_5$; R$^7$=R$^{13}$=CH$_3$ | Pale Yellow Solid | 201–203.5° C. | 3410 cm$^{-1}$ (N—H;m) 1672 cm$^{-1}$ (C=O;s) 750 cm$^{-1}$ (indole;s) | Consistent | Purple |
| 36 | 10.0 g 3-(4-Dimethylaminophenyl)-3-(1-benzyl-2-methylindol-3-yl)-phthalide | 10.0 g of 85 percent | 150.0 ml Ethoxyethanol | 100° C. | 6 hours | 6.4 g 4-(4-Dimethylaminophenyl)-4-(1-benzyl-2-methylindol-3-yl)-phthalazin-1(2H)—one | V: R=R$^1$=R$^8$=R$^{14}$=H; R$^6$=R$^{12}$=C$_8$H$_{17}$; R$^7$=R$^{13}$=CH$_3$; R$^{12}$=C$_6$H$_5$CH$_2$ | Pale Orange Solid | 155–165° C. | 3420 cm$^{-1}$ (N—H;s) 1667 cm$^{-1}$ (C=O;s) 750 cm$^{-1}$ (indole;s) | Consistent | Magenta |
| 37 | 15.0 g 3-(4-Dimethylaminophenyl)-3-(4-N—ethyl-N—benzylaminophenyl)-6-dimethylaminophthalide | 17.6 g of 85 percent | 225.0 ml 2-Ethoxyethanol | 100° C. | 2 hours | 13.0 g Of a mixture of 4-(4-dimethylaminophenyl)-4-(4-N—ethyl-N—benzylaminophenyl)-7-dimethylaminophthalazin-1(2H)—one and 3-(4-dimethylaminophenyl)-3-(4-N—ethyl-N—benzylaminophenyl)-6-dimethylaminophthalimidine | III & IV: R=N(CH$_3$)$_2$; R$^1$=R$^9$=H; R$^3$=R$^5$=H, R$^4$=R$^5$=R$^{10}$=R$^{11}$=CH$_3$ | Pale Blue-green Solid | 80–92° C. | 3420 cm$^{-1}$ (N—H;m) 1670 cm$^{-1}$ (C=O;m) | Consistent | Blue |

It is contemplated that by following the procedure described in the foregoing examples but employing the appropriate 3-(2-$R^3$-4-N-$R^4$-N-$R^5$-aminophenyl-5/6-R-phthalides with the appropriate $R^1$-substituted hydrazine of Formula XXIV, there will be obtained 3-$R^1$-4-[2-$R^3$-4-(N-$R^4$-N-$R^5$-amino)phenyl]-R-phthalazin-1(2H)-ones of Formula II wherein Y is hydrogen, presented in Examples 38–49, presented in Table D herein below.

It is contemplated that by following the procedure described in the foregoing examples but employing the appropriate 3-[2-$R^3$-4-(N-$R^4$-N-$R^5$-amino)phenyl]-3-(1-$R^{12}$-2-$R^{13}$-5/6-$R^{14}$-indol-3-yl)-5/6-R-phthalides with the appropriate $R^1$-substituted hydrazine of Formula XXIV, there will be obtained 3-$R^1$-4-[2-$R^3$-4-(N-$R^4$-N-$R^5$-amino)phenyl]-4-(1-$R^{12}$-2-$R^{13}$-5/6-$R^{14}$-indol-3-yl)-R-phthalazin-1(2H)-one of Formula IV, presented in Examples 62–73, presented in Table F hereinbelow.

TABLE D

| Example No. | R | $R^1$ | $R^3$ | $R^4$ | $R^5$ |
|---|---|---|---|---|---|
| 38 | N($C_2H_5$)$_2$ | 2-Cl$C_6H_4$ | $CH_3O$ | $C_3H_7$ | $C_3H_7$ |
| 39 | COO$C_4H_9$ | 4-Cl—2$CH_3C_6H_3$ | H | $C_4H_9$ | $C_4H_9$ |
| 40 | (Cl)$_4$ | 4-$CH_3OC_6H_4$ | $C_4H_9O$ | $CH_3$ | $CH_3$ |
| 41 | COO$C_8H_{17}$ | 3-$NO_2C_6H_4$ | $C_2H_5O$ | $C_2H_5$ | $C_2H_5$ |
| 42 | N($C_4H_9$)$_2$ | 4-$CH_3C_6H_4$ | $C_3H_7$ | $CH_3$ | $CH_3$ |
| 43 | COO$C_3H_7$ | H | H | $C_2H_5$ | $C_6H_5CH_2$ |
| 44 | COO$C_{16}H_{33}$ | 2,3-($NO_2$)$_2C_6H_3$ | H | $C_2H_5$ | $C_2H_5$ |
| 45 | COO$C_{12}H_{25}$ | 3-Br$C_6H_4$ | H | $CH_3$ | $CH_3$ |
| 46 | N($C_3H_7$)$_2$ | 3,4-(Cl)$_2C_6H_3$ | $C_3H_7O$ | $C_2H_5$ | $C_2H_5$ |
| 47 | H | 3-$NO_2C_6H_4$ | N($C_4H_9$)$_2$ | $C_4H_9$ | $C_4H_9$ |
| 48 | COO$C_6H_{13}$ | 4-Br$C_6H_4$ | $C_2H_5CONH$ | $CH_3$ | $CH_3$ |
| 49 | N($CH_3$)$_2$ | H | N($C_2H_5$)($C_6H_5CH_2$) | $C_2H_5$ | $C_6H_5CH_2$ |

TABLE F

| | Part 1 | | | | | Part 2 | | |
|---|---|---|---|---|---|---|---|---|
| Example No. | R | $R^1$ | $R^3$ | $R^4$ | $R^5$ | $R^{12}$ | $R^{13}$ | $R^{14}$ |
| 62 | N($C_4H_9$)$_2$ | 2-Br$C_6H_9$ | $C_4H_9CONH$ | $C_2H_5$ | $C_2H_5$ | $C_6H_5CH_2$ | $CH_3$ | H |
| 63 | COO$C_4H_9$ | 2-$NH_2C_6H_4$ | H | $C_2H_5$ | $C_6H_5CH_2$ | $C_8H_{17}$ | $C_2H_5$ | H |
| 64 | COO$C_{12}H_{25}$ | 2-Cl$C_6H_4$ | $C_2H_5O$ | $C_4H_9$ | $C_4H_9$ | $C_6H_{13}$ | $C_6H_5$ | 5-$CH_3$ |
| 65 | N($C_3H_7$)$_2$ | 3,5-$Cl_2C_6H_3$ | $C_3H_7CONH$ | $CH_3$ | $CH_3$ | $C_{16}H_{33}$ | $C_2H_5$ | 5-$CH_3$ |
| 66 | N($C_2H_5$)$_2$ | 3-Cl$C_6H_4$ | $C_4H_9O$ | $CH_3$ | 4-$CH_3C_6H_4$ | $C_{12}H_{25}$ | $C_2H_5$ | 5-Br, 6-$NO_2$ |
| 67 | COO$C_6H_{13}$ | $CH_3$ | N($CH_3$)$_2$ | $CH_3$ | $CH_3$ | $CH_3CHCH$ | $CH_3$ | 6-Br |
| 68 | COO$C_{10}H_{21}$ | 2,6-$Cl_2C_6H_3$ | H | $C_2H_5$ | 4-$CH_3C_6H_4CH_2$ | $CH_3$ | $CH_3$ | 6-$NO_2$ |
| 69 | COOH | H | $C_3H_7O$ | $C_2H_5$ | $C_2H_5$ | $C_4H_9$ | H | 5-$CH_3O$ |
| 70 | N($CH_3$)$_2$ | 4-Br$C_6H_4$ | N($C_2H_5$)$_2$ | $C_2H_5$ | $C_2H_5$ | $C_6H_{13}$ | $C_6H_5$ | 6-Cl |
| 71 | (Cl)$_2$ | 4-$NO_2C_6H_4$ | $C_4H_9O$ | $C_2H_5$ | 4-Cl$C_6H_4CH_2$ | $CH_3$ | $C_3H_7$ | H |
| 72 | COO$CH_3$ | 3-$CH_3C_6H_4$ | H | $CH_3$ | $CH_3$ | $CH_2CH$ | $CH_3$ | H |
| 73 | COOH$C_{16}H_{33}$ | H | $CH_3O$ | $C_4H_9$ | $C_4H_9$ | 2-F$C_6H_4CH_2$ | $CH_3$ | H |

It is contemplated that by following the procedure described in the foregoing examples but employing the appropriate 3-[2-$R^3$-4-(N-$R^4$-N-$R^5$-amino)phenyl]-3-[2-$R^9$-4-(N-$R^{10}$-N-$R^{11}$-amino)phenyl]-5/6-R-phthalides with the appropriate $R^1$-substituted hydrazine of Formula XXIV, there will be obtained 3-$R^1$-4-[2-$R^3$-4-(N-$R^4$-N-$R^5$-amino)phenyl]-4-[2-$R^3$-4-(N-$R^4$-N-$R^5$-amino)phenyl]-R-phthalazin-1(2H)-ones of Formula III, presented in Examples 50–61, presented in Table E hereinbelow.

It is contemplated that by following the procedure described in the foregoing examples but employing the appropriate 3-(1-$R^6$-2-$R^7$-5/6-$R^8$-indol-3-yl)-3-(1-$R^{12}$-2-$R^{13}$-5/6-$R^{14}$-indol-3-yl)-5/6-R-phthalides with the appropriate $R^1$-substituted hydrazine of Formula XXIV, there will be obtained 3-$R^1$-4-(1-$R^6$-2-$R^7$-5/6-$R^8$-indol-3-yl)-4-(1-$R^{12}$-2-$R^{13}$-5/6-$R^{14}$-indol-3-yl)-R-phthalazin-1(2H)-one of Formula V, presented in Examples 74–85, presented in Table G hereinbelow.

TABLE E

| | Part 1 | | | | | Part 2 | | |
|---|---|---|---|---|---|---|---|---|
| Example No. | R | $R^1$ | $R^3$ | $R^4$ | $R^5$ | $R^9$ | $R^{10}$ | $R^{11}$ |
| 50 | N($C_2H_5$)$_2$ | 2-Cl$C_6H_4$ | $CH_3O$ | $C_3H_7$ | $C_3H_7$ | H | $C_2H_5$ | 4-$CH_3C_6H_3CH_2$ |
| 51 | COO$C_4H_9$ | 4-Cl—2$CH_3C_6H_3$ | H | $C_4H_9$ | $C_4H_9$ | $C_3H_7O$ | $C_2H_5$ | $C_2H_5$ |
| 52 | H | 4-$CH_3OC_6H_4$ | $C_4H_9O$ | $CH_3$ | $CH_3$ | H | $C_4H_9$ | $C_4H_9$ |
| 53 | COO$C_8H_{17}$ | 3-$NO_2C_6H_4$ | $C_2H_5O$ | $C_2H_5$ | $C_2H_5$ | $C_2H_5CONH$ | $CH_3$ | $CH_3$ |
| 54 | N($C_4H_9$)$_2$ | 4-$CH_3C_6H_4$ | $C_3H_7$ | $CH_3$ | $CH_3$ | $C_2H_5O$ | $C_3H_7$ | $C_3H_7$ |
| 55 | COO$C_3H_7$ | H | H | $C_2H_5$ | $C_6H_5CH_2$ | H | $CH_3$ | 4-Cl$C_6H_4CH_2$ |
| 56 | COO$C_{16}H_{33}$ | 2,4-($NO_2$)$_2C_6H_3$ | H | $C_2H_5$ | $C_2H_5$ | H | $C_2H_5$ | $C_2H_5$ |
| 57 | COO$C_{12}H_{25}$ | 3-Br$C_6H_4$ | H | $CH_3$ | $CH_3$ | N($CH_3$)$_2$ | $CH_3$ | $CH_3$ |
| 58 | N($C_3H_7$)$_2$ | 3,4-(Cl)$_2C_6H_3$ | $C_3H_7O$ | $C_2H_5$ | $C_2H_5$ | $C_3H_7CONH$ | $C_2H_5$ | $C_2H_5$ |
| 59 | (Br)$_4$ | 3-$NO_2C_6H_4$ | N($C_4H_9$)$_2$ | $C_4H_9$ | $C_4H_9$ | $C_4H_9O$ | $CH_3$ | $CH_3$ |
| 60 | COO$C_6H_{13}$ | 4-Br$C_6H_4$ | $C_2H_5CONH$ | $CH_3$ | $CH_3$ | $CH_3O$ | $C_4H_9$ | $C_4H_9$ |
| 61 | N($CH_3$)$_2$ | H | N($C_2H_5$)($C_6H_5CH_2$) | $C_2H_5$ | $C_6H_5CH_2$ | H | $C_2H_5$ | $C_2H_5$ |

TABLE G

| | Part 1 | | | | | Part 2 | | |
|---|---|---|---|---|---|---|---|---|
| Example No. | R | $R^1$ | $R^6$ | $R^7$ | $R^8$ | $R^{12}$ | $R^{13}$ | $R^{14}$ |
| 74 | N($C_2H_5$)$_2$ | 2-$CH_3C_6H_4$ | $C_3H_7$ | | $C_6H_5$ 6-Cl | 3-Cl$C_6H_4CH_2$ | $C_2H_5$ | H |

TABLE G-continued

| | Part 1 | | | | Part 2 | | |
|---|---|---|---|---|---|---|---|
| Example No. | R | $R^1$ | $R^6$ | $R^7$ | $R^8$ | $R^{12}$ | $R^{13}$ $R^{14}$ |
| 75 | $N(C_4H_9)_2$ | $3\text{-}BrC_6H_4$ | $2\text{-}FC_6H_4CH_2$ | $CH_3$ | H | $C_8H_{17}$ | $CH_3$ H |
| 76 | $COOC_6H_{13}$ | $2\text{-}NH_2C_6H_4$ | $C_4H_9$ | H | $5,6\text{-}(CH_3O)_2$ | $C_5H_{11}$ | H H |
| 77 | $COOC_{16}H_{33}$ | H | $C_6H_5CH_2$ | H | 6-F | $C_2H_5$ | $CH_3$ $5,6\text{-}(CH_3)_2$ |
| 78 | H | $3,4\text{-}Cl_2C_6H_3$ | H | $C_2H_5$ | H | $4\text{-}ClC_6H_4CH_2$ | $CH_3$ $5\text{-}NO_2$ |
| 79 | COOH | $4\text{-}CH_3OC_6H_4$ | $CH_3$ | $CH_3$ | $5\text{-}NO_2$ | $C_4H_9$ | H $5\text{-}CH_3O$ |
| 80 | $COOC_8H_{17}$ | $4\text{-}CH_3C_6H_4$ | $C_6H_5OC_2H_4$ | $C_2H_5$ | $5\text{-}CH_3$ | $CH_2CH$ | $CH_3$ H |
| 81 | $N(C_3H_7)_2$ | $4\text{-}NO_2C_6H_4$ | $C_6H_{13}$ | H | H | $2,6\text{-}Cl_2C_6H_3CH_2$ | $CH_3$ H |
| 82 | $N(C_2H_5)_2$ | H | H | $C_6H_5$ | 6-Cl | $C_6H_5CH_2$ | H 5-Cl |
| 83 | $N(C_4H_9)_2$ | $CH_3$ | $CH_3CHCH$ | $CH_2$ | H | $C_{16}H_{33}$ | $CH_3$ H |
| 84 | $COOC_{12}H_{25}$ | $C_6H_5$ | $CH_3$ | H | $5\text{-}Br, 6\text{-}NO_2$ | $C_2H_5$ | $C_3H_7$ H |
| 85 | $COOCH_3$ | $2\text{-}ClC_6H_4$ | $C_8H_{17}$ | H | 5-I | $C_2H_5$ | $CH_3$ $5,6\text{-}(CH_3)_2$ |

It is contemplated that by following the procedure described in the foregoing examples but employing the appropriate 3-[2-$R^3$-4-(N-$R^4$-N-$R^5$-amino)phenyl]-3-[2-$R^9$-4-(N-$R^{10}$-N-$R^{11}$-amino)phenyl]-5/6-R-phthalides with the appropriate $R^1$-substituted hydrazine of Formula XXIV, there will be obtained 2-($R^1$-amino)-3-[2-$R^3$-4-(N-$R^4$-N-$R^5$-amino)pheny]-3-(1-$R^{12}$-2-$R^{13}$-5/6-$R^{14}$-indol-3-yl)-6-R-phthalimidine of Formula XV, presented in Examples 98–109, presented in Table I hereinbelow.

TABLE I

| | Part 1 | | | | Part 2 | | |
|---|---|---|---|---|---|---|---|
| Example No. | R | $R^1$ | $R^3$ | $R^4$ $R^5$ | $R^{12}$ | $R^{13}$ $R^{14}$ |
| 98 | $N(C_4H_9)_2$ | $2\text{-}BrC_6H_4$ | $C_4H_9CONH$ | $C_2H_5$ $C_2H_5$ | $C_6H_5CH_2$ | $CH_3$ H |
| 99 | $COOC_4H_9$ | $2\text{-}NH_2C_6H_4$ | H | $C_2H_5$ $C_6H_5CH_2$ | $C_8H_{17}$ | $C_2H_5$ H |
| 100 | $COOC_{12}H_{25}$ | $2\text{-}ClC_6H_4$ | $C_2H_5O$ | $C_4H_9$ $C_4H_9$ | $C_6H_{13}$ | $C_6H_5$ $5\text{-}CH_3$ |
| 101 | $N(C_3H_7)_2$ | $3,5\text{-}Cl_2C_6H_3$ | $C_3H_7CONH$ | $CH_3$ $CH_3$ | $C_{16}H_{33}$ | $C_2H_5$ $5\text{-}CH_3$ |
| 102 | $N(C_2H_5)_2$ | $3\text{-}ClC_6H_3$ | $C_4H_9O$ | $CH_3$ $4\text{-}CH_3C_6H_4$ | $C_{12}H_{25}$ | $C_2H_5$ $5\text{-}Br, 6\text{-}NO_2$ |
| 103 | $COOC_6H_{13}$ | $CH_3$ | $N(CH_3)_2$ | $CH_3$ $CH_3$ | $CH_3CHCH$ | $CH_3$ 6-Br |
| 104 | $COOC_{10}H_{21}$ | $2,6\text{-}Cl_2C_6H_3$ | H | $C_2H_5$ $4\text{-}CH_3C_6H_4CH_2$ | $CH_3$ | $CH_3$ $6\text{-}NO_2$ |
| 105 | COOH | H | $C_3H_7O$ | $C_2H_5$ $C_2H_5$ | $C_4H_9$ | H $5\text{-}CH_3O$ |
| 106 | $N(CH_3)_2$ | $4\text{-}BrC_6H_4$ | $N(C_2H_5)_2$ | $C_2H_5$ $C_2H_5$ | $C_6H_{13}$ | $C_6H_5$ 6-Cl |
| 107 | H | $4\text{-}NO_2C_6H_4$ | $C_4H_9O$ | $C_2H_5$ $4\text{-}ClC_6H_4CH_2$ | $CH_3$ | $C_3H_7$ H |
| 108 | $COOCH_3$ | $3\text{-}CH_3C_6H_4$ | H | $CH_3$ $CH_3$ | $CH_2CH$ | $CH_3$ H |
| 109 | $COOHC_{16}H_{33}$ | H | $CH_3O$ | $C_4H_9$ $C_4H_9$ | $2\text{-}FC_6H_4CH_2$ | $CH_3$ H | mula XXIV, there will be obtained 2-($R^1$-amino)-3-[2-$R^2$-4-(N-$R^4$-N-$R^5$-amino)phenyl]-3-[2-$R^9$-4-(N-$R^{10}$-N-$R^{11}$-amino)phenyl]-6-R-phthalimidine of Formula XVI, presented in Examples 86–97, presented in Table H hereinbelow.

It is contemplated that by following the procedure described in the foregoing examples but employing the appropriate 3-(1-$R^6$-2-$R^7$-5/6-$R^8$-indol-3-yl)-3-(1-$R^{12}$-2-$R^{13}$-5/6-$R^{14}$-indol-3-yl)-5/6-R-phthalides with the appropriate $R^1$-substituted hydrazine of Formula XXIV,

TABLE H

| | Part 1 | | | | | Part 2 | |
|---|---|---|---|---|---|---|---|
| Example No. | R | $R^1$ | $R^3$ | $R^4$ | $R^5$ | $R^9$ | $R^{10}$ $R^{11}$ |
| 86 | $N(C_2H_5)_2$ | $2\text{-}ClC_6H_4$ | $CH_3O$ | $C_3H_7$ | $C_3H_7$ | H | $C_2H_5$ $4\text{-}CH_3C_6H_4CH_2$ |
| 87 | $COOC_4H_9$ | $4\text{-}Cl-2\text{-}CH_3C_6H_3$ | H | $C_4H_9$ | $C_4H_9$ | $C_3H_7O$ | $C_2H_5$ $C_2H_5$ |
| 88 | $(Cl)_4$ | $4\text{-}CH_3OC_6H_4$ | $C_4H_9O$ | $CH_3$ | $CH_3$ | H | $C_4H_9$ $C_4H_9$ |
| 89 | $COOC_8H_{17}$ | $3\text{-}NO_2C_6H_4$ | $C_2H_5O$ | $C_2H_5$ | $C_2H_5$ | $C_2H_5CONH$ | $CH_3$ $CH_3$ |
| 90 | $N(C_4H_9)_2$ | $4\text{-}CH_3C_6H_4$ | $C_3H_7$ | $CH_3$ | $CH_3$ | $C_2H_5O$ | $C_3H_7$ $C_3H_7$ |
| 91 | $COOC_3H_7$ | H | H | $C_2H_5$ | $C_6H_5CH_2$ | H | $CH_3$ $4\text{-}ClC_6H_4CH_2$ |
| 92 | $COOC_{16}H_{33}$ | $2,4\text{-}(NO_2)_2C_6H_3$ | H | $C_2H_5$ | $C_2H_5$ | H | $C_2H_5$ $C_2H_5$ |
| 93 | $COOC_{12}H_{25}$ | $3\text{-}BrC_6H_4$ | H | $CH_3$ | $CH_3$ | $N(CH_3)_2$ | $CH_3$ $CH_3$ |
| 94 | $N(C_3H_7)_2$ | $3,4\text{-}(Cl)_2C_6H_3$ | $C_3H_7O$ | $C_2H_5$ | $C_2H_5$ | $C_3H_7CONH$ | $C_2H_5$ $C_2H_5$ |
| 95 | H | $3\text{-}NO_2C_6H_4$ | $N(C_4H_9)_2$ | $C_4H_9$ | $C_4H_9$ | $C_4N_9O$ | $CH_3$ $CH_3$ |
| 96 | $COOC_6H_{13}$ | $4\text{-}BrC_6H_4$ | $C_2H_5CONH$ | $CH_3$ | $CH_3$ | $CH_3O$ | $C_4H_9$ $C_4H_9$ |
| 97 | $N(CH_3)_2$ | H | $N(C_2H_5)(C_6H_5CH_2)$ | $C_2H_5$ | $C_6H_5CH_2$ | H | $C_2H_5$ $C_2H_5$ |

It is contemplated that by following the procedure described in the foregoing examples but employing the appropriate 3-[2-$R^3$-4-(N-$R^4$-N-$R^5$-amino)phenyl]-3-(1-$R^{12}$-2-$R^{13}$-5/6-$R^{14}$-indol-3-yl)-5/6-R-phthalides with the appropriate $R^1$-substituted hydrazine of Formula XXIV, there will be obtained 2-($R^1$-amino)-3-(1-$R^6$-2-$R^7$-5/6-$R^8$-indol-3-yl)-3-(1-$R^{12}$-2-$R^{13}$-5/6-$R^{14}$-indol-3-yl)-6-R-phthalimidine of Formula XVI, presented in Examples 110–121, presented in Table J hereinbelow.

TABLE J

| | Part 1 | | | | Part 2 | | |
|---|---|---|---|---|---|---|---|
| Example No. | R | $R^1$ | $R^6$ | $R^7$ | $R^8$ | $R^{12}$ | $R^{13}$ $R^{14}$ |
| 110 | $N(C_2H_5)_2$ | $2\text{-}CH_3C_6H_4$ | $C_3H_7$ | $C_6H_5$ | 6-Cl | $3\text{-}ClC_6H_4CH_2$ | $C_2H_5$ H |
| 111 | $N(C_4H_9)_2$ | $3\text{-}BrC_6H_4$ | $2\text{-}FC_6H_4CH_2$ | $CH_3$ | H | $C_8H_{17}$ | $CH_3$ H |
| 112 | $COOC_6H_{13}$ | $2\text{-}NH_2C_6H_4$ | $C_4H_9$ | H | $5,6\text{-}(CH_3O)_2$ | $C_5H_{11}$ | H H |
| 113 | $COOC_{16}H_{33}$ | H | $C_6H_5CH_2$ | H | 6-F | $C_2H_5$ | $CH_3$ $5,6\text{-}(CH_3)_2$ |
| 114 | $(Cl)_4$ | $3,4\text{-}Cl_2C_6H_3$ | H | $C_2H_5$ | H | $4\text{-}ClC_6H_4CH_2$ | $CH_3$ $5\text{-}NO_2$ |
| 115 | COOH | $4\text{-}CH_3OC_6H_4$ | $CH_3$ | $CH_3$ | $5\text{-}NO_2$ | $C_4H_9$ | H $5\text{-}CH_3O$ |

TABLE J-continued

| Example No. | Part 1 | | | | Part 2 | | | |
|---|---|---|---|---|---|---|---|---|
| | R | $R^1$ | $R^6$ | $R^7$ | $R^8$ | $R^{12}$ | $R^{13}$ | $R^{14}$ |
| 116 | $COOC_8H_{17}$ | $4\text{-}CH_3C_6H_4$ | $C_4H_9$ | $C_2H_5$ | 5-$CH_3$ | $CH_2CH$ | $CH_3$ | H |
| 117 | $N(C_3H_7)_2$ | $4\text{-}NO_2C_6H_4$ | $C_6H_{13}$ | H | H | $2,6\text{-}Cl_2C_6H_3CH_2$ | $CH_3$ | H |
| 118 | $N(C_2H_5)_2$ | H | H | $C_6H_5$ | 6-Cl | $C_6H_5CH_2$ | H | 5-Cl |
| 119 | $N(C_4H_9)_2$ | $CH_3$ | $CH_3CHCH$ | $CH_3$ | H | $C_{16}H_{33}$ | $CH_3$ | H |
| 120 | $COOC_{12}H_{25}$ | $C_6H_5$ | $CH_3$ | H | 5-Br, 6-$NO_2$ | $C_2H_5$ | $C_3H_7$ | H |
| 121 | $COOCH_3$ | $2\text{-}ClC_6H_4$ | $C_8H_{17}$ | H | 5-I | $C_2H_5$ | $CH_3$ | 5,6-$(CH_3)_2$ |

It is contemplated that by following the procedure described in the foregoing examples but employing the appropriate isomeric mixture of 7-[2-$R^3$-4-(N-$R^4$-N-$R^5$-amino)-phenyl]-7-(1-$R^{12}$-2-$R^{13}$-5/6-$R^{14}$-indol-3-yl)-furo-(3,4b)-pyridine-5(7H)-one and 5-[2-$R^3$-4-(N-$R^4$-N-$R^5$-amino)phenyl]-5-(1-$R^{12}$-2-$R^{13}$-5/6-$R^{14}$-indolyl)-(3,4b)-pyridine-7(5H)-one with the appropriate $R^1$-substituted hydrazine of Formula XXIV, there will be obtained an isomeric mixture of $R^1$-8-[2-$R^3$-4-(N-$R^4$-N-$R^5$-amino)phenyl]-7-(1-$R^{12}$-2-$R^{13}$-5/6-$R^{14}$-indol-3-yl)pyrido-[2,3d]-pyridazin-5(6H)-ones and R-5-[2-$R^3$-4-(N-$R^4$-N-$R^5$-amino)phenyl]-5-(1-$R^{12}$-2-$R^{13}$-$R^{14}$-indol-3-yl)-6-$R^1$-pyrido-[2,3d]-pyridazin-8(5H)-ones of Formulas VIII and IX, presented in Examples 122–133, presented in Table K hereinbelow.

TABLE K

| Example No. | Part 1 | | | | Part 2 | | |
|---|---|---|---|---|---|---|---|
| | $R^1$ | $R^3$ | $R^4$ | $R^5$ | $R^{12}$ | $R^{13}$ | $R^{14}$ |
| 122 | $2\text{-}BrC_6H_4$ | $C_4H_9CONH$ | $C_2H_5$ | $C_2H_5$ | $C_6H_5CH_2$ | $CH_3$ | H |
| 123 | $2\text{-}NH_2C_6H_4$ | H | $C_2H_5$ | $C_6H_5CH_2$ | $C_8H_{17}$ | $C_2H_5$ | H |
| 124 | $2\text{-}ClC_6H_4$ | $C_2H_5O$ | $C_4H_9$ | $C_4H_9$ | $C_6H_{13}$ | $C_6H_5$ | 5-$CH_3$ |
| 125 | $3,5\text{-}Cl_2C_6H_3$ | $C_3H_7CONH$ | $CH_3$ | $CH_3$ | $C_{16}H_{33}$ | $C_2H_5$ | 5-$CH_3$ |
| 126 | $3\text{-}ClC_6H_3$ | $C_4H_9O$ | $CH_3$ | $4\text{-}CH_3C_6H_4CH_2$ | $C_{12}H_{25}$ | $C_2H_5$ | 5-Br, 6-$NO_2$ |
| 127 | $CH_3$ | $N(CH_3)_2$ | $CH_3$ | $CH_3$ | $CH_3CHCH$ | $CH_3$ | 6-Br |
| 128 | $2,6\text{-}Cl_2C_6H_3$ | H | $C_2H_5$ | $4\text{-}CH_3C_6H_4CH_2$ | $CH_3$ | $CH_3$ | 6-$NO_2$ |
| 129 | H | $C_3H_7O$ | $C_2H_5$ | $C_2H_5$ | $C_4H_9$ | H | 5-$CH_3O$ |
| 130 | $4\text{-}BrC_6H_4$ | $N(C_2H_5)_2$ | $C_2H_5$ | $C_2H_5$ | $C_6H_{13}$ | $C_6H_5$ | 6-Cl |
| 131 | $4\text{-}NO_2C_6H_4$ | $C_4H_9O$ | $C_2H_5$ | $4\text{-}ClC_6H_4CH_2$ | $CH_3$ | $C_3H_7$ | H |
| 132 | $3\text{-}CH_3C_6H_4$ | H | $CH_3$ | $CH_3$ | $CH_2CH$ | $CH_3$ | H |
| 133 | H | $CH_3O$ | $C_4H_9$ | $C_4H_9$ | $2\text{-}FC_6H_4CH_2$ | $CH_3$ | H |

It is contemplated that by following the procedure described in the foregoing examples but employing the appropriate isomeric mixture of 7-(1-$R^6$-2-$R^7$-5/6-$R^8$-indol-3-yl)-7-(1-$R^{12}$-2-$R^{13}$-5/6-$R^{14}$-indol-3-yl)-furo-(3,4b)-pyridin-5(7H)-one and 5-(1-$R^6$-2-$R^7$-5/6-$R^8$-indol-3-yl)-5-(1-$R^{12}$-2-$R^{13}$-5/6-$R^{14}$-indolyl)-(3,4b)-pyridin-7(5H)-one with the appropriate $R^1$-substituted hydrazine of Formula XXIV, there will be obtained an isomeric mixture of 2/3-R-7-$R^1$-8-(1-$R^6$-2-$R^7$-5/6-$R^8$-indol-3-yl)-8-(1-$R^{12}$-2-$R^{13}$-5/6-$R^{14}$-indol-3-yl)pyrido-[2,3d]-pyridazin-5(6H)-ones and 5-(1-$R^6$-2-$R^7$-5/6-$R^8$-indol-3-yl)-5-(1-$R^{12}$-2-$R^{13}$-3-$R^{14}$-indol-3-yl)-6-$R^1$-pyrido-[2,3d]-pyridazin-8(5H)-ones of Formulas X and XI, presented in Table L hereinbelow.

TABLE L

| Example No. | Part 1 | | | | Part 2 | | |
|---|---|---|---|---|---|---|---|
| | $R^1$ | $R^6$ | $R^7$ | $R^8$ | $R^{12}$ | $R^{13}$ | $R^{14}$ |
| 134 | $2\text{-}CH_3C_6H_4$ | $C_3H_7$ | $C_6H_5$ | 6-Cl | $3\text{-}ClC_6H_4CH_2$ | $C_2H_5$ | H |
| 135 | $3\text{-}BrC_6H_4$ | $2\text{-}FC_6H_4CH_2$ | $CH_3$ | H | $C_8H_{17}$ | $CH_3$ | H |
| 136 | $2\text{-}NH_2C_6H_4$ | $C_4H_9$ | H | 5,6-$(CH_3O)_2$ | $C_5H_{11}$ | H | H |
| 137 | H | $C_6H_5CH_2$ | H | 6-F | $C_2H_5$ | $CH_3$ | 5,6-$(CH_3)_2$ |
| 138 | $3,4\text{-}Cl_2C_6H_3$ | H | $C_2H_5$ | H | $4\text{-}ClC_6H_4CH_2$ | $CH_3$ | 5-$NO_2$ |
| 139 | $4\text{-}CH_3OC_6H_4$ | $CH_3$ | $CH_3$ | 5-$NO_2$ | $C_4H_9$ | H | 5-$CH_3O$ |
| 140 | $4\text{-}CH_3C_6H_4$ | $C_4H_9$ | $C_2H_5$ | 5-$CH_3$ | $CH_2CH$ | $CH_3$ | H |
| 141 | $4\text{-}NO_2C_6H_4$ | $C_6H_{13}$ | H | H | $6\text{-}Cl_2C_6H_3CH_2$ | $CH_3$ | H |
| 142 | H | H | $C_6H_5$ | 6-Cl | $C_6H_5CH_2$ | H | 5-Cl |
| 143 | $CH_3$ | $CH_3CHCH$ | $CH_3$ | H | $C_{16}H_{33}$ | $CH_3$ | H |
| 144 | $C_6H_5$ | $CH_3$ | H | 5-Br, 6-$NO_2$ | $C_2H_5$ | $C_3H_7$ | H |
| 145 | $2\text{-}ClC_6H_4$ | $C_8H_{17}$ | H | 5-I | $C_2H_5$ | $CH_3$ | 5,6-$(CH_3)_2$ |

What is claimed is:

1. A substrate for use in electrochromic recording comprising a support sheet containing as a color-forming substance a 3-$R^1$-4-X-4-Y-R-phthalazin-1(2H)-one having the structural formula

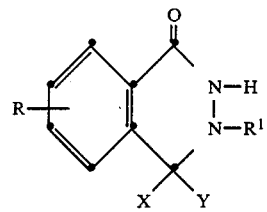

wherein:
R represents hydrogen, dialkylamino in which alkyl is non-tertiary $C_1$ to $C_4$ alkyl, $COOR^2$ in which $R^2$ is hydrogen or non-tertiary $C_1$ to $C_{16}$ alkyl or one to four halo;
$R^1$ represents hydrogen, $C_1$ to $C_3$ alkyl, pyridyl,

in which Z is non-tertiary $C_1$ to $C_4$ alkoxy, $NHNH_2$, or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino;

X is selected from the group consisting of

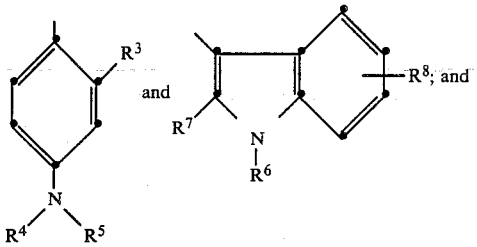

Y is selected from the group consisting of hydrogen,

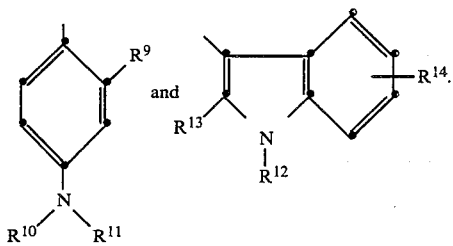

in which $R^3$ and $R^9$ independently represent hydrogen, non-tertiary $C_1$ to $C_4$ alkyl, non-tertiary $C_1$ to $C_4$ alkoxy, acylamido in which acyl is non-tertiary $C_2$ to $C_4$ alkyl or dialkylamino in which alkyl is non-tertiary $C_1$ to $C_4$ alkyl, $R^4$ and $R^{10}$ independently represent non-tertiary $C_1$ to $C_4$ alkyl, benzyl or benzyl substituted in the benzene ring by one or two of halo or $C_1$ to $C_3$ alkyl, $R^5$ and $R^{11}$ independently represent non-tertiary $C_1$ to $C_4$ alkyl, benzyl or benzyl substituted in the benzene ring by one or two of halo or $C_1$ to $C_3$ alkyl, $R^6$ and $R^{12}$ independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or $C_1$ to $C_3$ alkyl, $R^7$ and $R^{13}$ independently represent hydrogen, $C_1$ to $C_3$ alkyl or phenyl, and $R^8$ and $R^{14}$ independently represent hydrogen, halo, non-tertiary $C_1$ to $C_4$ alkyl, non-tertiary $C_1$ to $C_4$ alkoxy or nitro.

2. A substrate for use in electrochromic recording according to claim 1 comprising a support sheet containing as a color-forming substance a 3-$R^1$-4-Y-4-[2-$R^3$-4-(N-$R^4$-N-$R^5$-amino)phenyl]-R-phthalazin-1(2H)-one having the structural formula

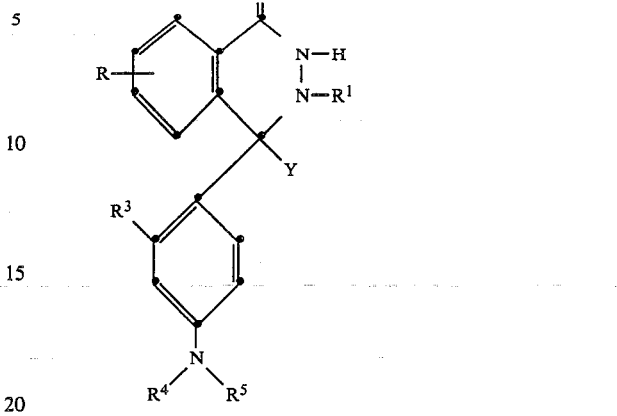

in which R, $R^1$, $R^3$, $R^4$, $R^5$ and Y each have the same respective meanings given in claim 1.

3. A substrate for use in electrochromic recording according to claim 2 comprising a support sheet containing as a color-forming substance a 3-$R^1$-4-[2-$R^3$-4-(N-$R^4$-N-$R^5$-amino)phenyl]-R-phthalazin-1(2H)-one having the structural formula

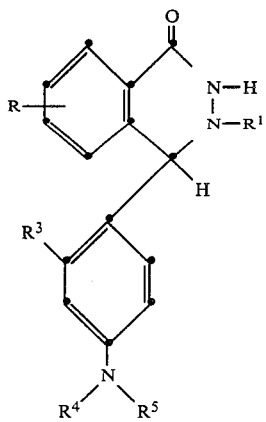

in which R, $R^1$, $R^3$, $R^4$ and $R^5$ each have the same respective meanings given in claim 2.

4. A substrate for use in electrochromic recording according to claim 1 comprising a support sheet containing as a color-forming substance a 3-$R^1$-[2-$R^3$-4-(N-$R^4$-N-$R^5$-amino)phenyl]-4-[2-$R^9$-4-(N-$R^{10}$-N-$R^{11}$-amino)phenyl]-R-phthalazin-1(2H)-one having the structural formula

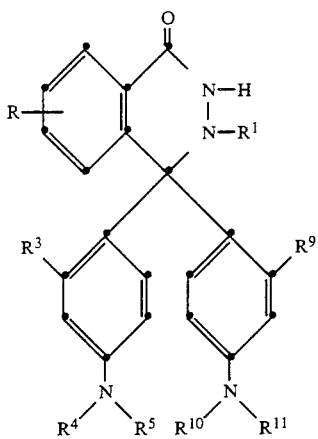

in which R, $R^1$, $R^3$, $R^4$, $R^5$, $R^9$, $R^{10}$ and $R^{11}$ each have the same respective meanings given in claim 1.

5. A substrate for use in electrochromic recording according to claim 1 comprising a support sheet containing as a color-forming substance a 3-$R^1$-4-[2-$R^3$-4-(N-$R^4$-N-$R^5$-amino)phenyl]-4-(1-$R^{12}$-2-$R^{13}$-5/6-$R^{14}$-indol-3-yl)-R-phthalazin-1(2H)-one having the structural formula

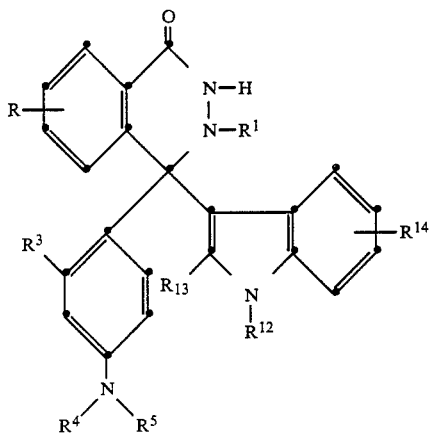

in which R, $R^1$, $R^3$, $R^4$, $R^5$, $R^{12}$, $R^{13}$ and $R^{14}$ each have the same respective meanings given in claim 1.

6. A substrate for use in electrochromic recording according to claim 1 comprising a support sheet containing as a color-forming substance a 3-$R^1$-4-(1-$R^6$-2-$R^7$-5/6-$R^8$-indol-3-yl)-4-(1-$R^{12}$-2-$R^{13}$-5/6-$R^{14}$-indol-3-yl)-R-phthalazin-1(2H)-one having the structural formula

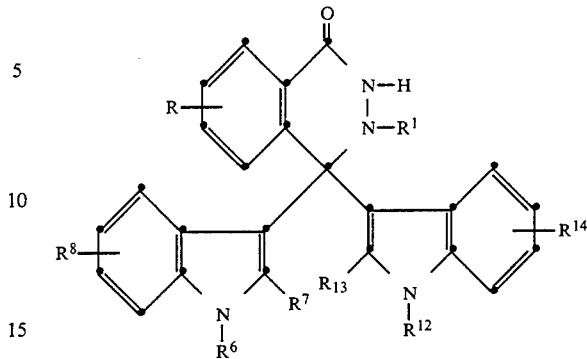

in which R, $R^1$, $R^6$, $R^7$, $R^8$, $R^{12}$, $R^{13}$ and $R^{14}$ each have the same respective meanings given in claim 1.

7. A substrate for use in electrochromic recording comprising a support sheet containing as color-forming substances an isomeric mixture of 7-$R^1$-8-X-8-Y-pyrido-[2,3d]-pyridazin-5(6H)-ones and 5-X-5-Y-6-$R^1$-pyrido-[2,3d]-pyridazin-8-(5H)-ones having the structural formulas

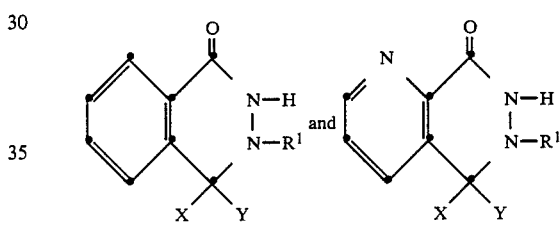

wherein:
$R^1$ represents hydrogen, $C_1$ to $C_3$ alkyl, pyridyl,

in which Z is non-tertiary $C_1$ to $C_4$ alkoxy, $NHNH_2$, or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino;

X is selected from the group consisting of

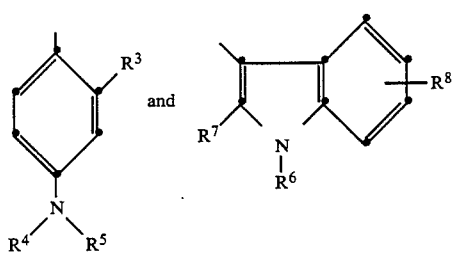

Y is selected from the group consisting of hydrogen,

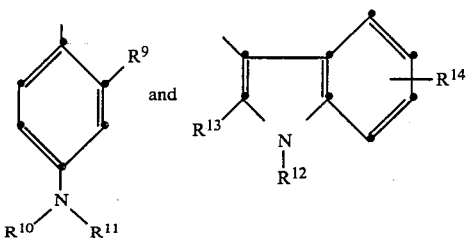

in which

R³ and R⁹ independently represent hydrogen, non-tertiary $C_1$ to $C_4$ alkyl, non-tertiary $C_1$ to $C_4$ alkoxy, acylamido in which acyl is non-tertiary $C_2$ to $C_4$ alkyl or dialkylamino in which alkyl is non-tertiary $C_1$ to $C_4$ alkyl, R⁴ and R¹⁰ independently represent non-tertiary $C_1$ to $C_4$ alkyl, benzyl or benzyl substituted in the benzene ring by one or two of halo or $C_1$ to $C_3$ alkyl, R⁵ and R¹¹ independently represent non-tertiary $C_1$ to $C_4$ alkyl, benzyl or benzyl substituted in the benzene ring by one or two of halo or $C_1$ to $C_3$ alkyl, R⁶ and R¹² independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or $C_1$ to $C_3$ alkyl, R⁷ and R¹³ independently represent hydrogen, $C_1$ to $C_3$ alkyl or phenyl, and R⁸ and R¹⁴ independently represent hydrogen, halo, non-tertiary $C_1$ to $C_4$ alkyl, non-tertiary $C_1$ to $C_4$ alkoxy or nitro.

8. A substrate for use in electrochromic recording according to claim 7 comprising a support sheet containing as color-forming substances an isomeric mixture of 7-R¹-8-[2-R³-4-(N-R⁴-N-R⁵-amino)phenyl]-8-(1-R¹²-2-R¹³-5/6-R¹⁴-indol-3-yl)-pyrido-[2,3d]-pyridazin-5(6H)-ones and 5-[2-R³-4-(N-R⁴-N-R⁵-amino)phenyl]-5-(1-R¹²-2-R¹³-5/6-R¹⁴-indol-3-yl)-6-R¹-pyrido-[2,3d]-pyridazin-8(5H)-ones having the structural formulas

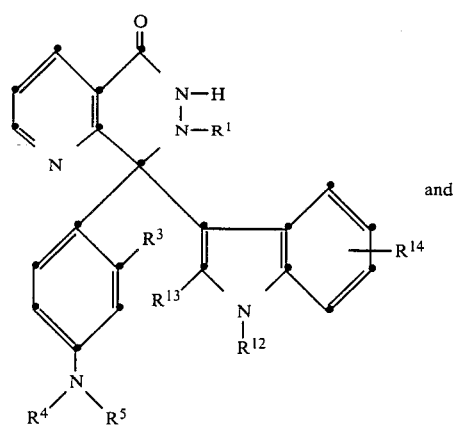

and

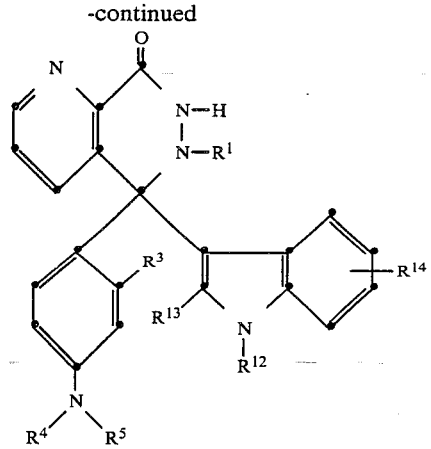

in which R¹, R³, R⁴, R⁵, R¹², R¹³ and R¹⁴ each have the same respective meanings given in claim 7.

9. A substrate for use in electrochromic recording according to claim 7 comprising a support sheet containing as color-forming substances isomeric mixtures of 7-R¹-8-(1-R⁶-2-R⁷-5/6-R⁸-indol-3-yl)-8-(1-R¹²-2-R¹³-5/6-R¹⁴-indol-3-yl)-pyrido-[P2,3d]-pyridazin-5(6H)-ones and 5-(1-R⁶-2-R⁷-5/6-R⁸-indol-3-yl)-5-(1-R¹²-2-R¹³-5/6-R¹⁴-indol-3-yl)-6-R¹-pyrido-[2,3d]-pyridazin-8(5H)-ones having the structural formulas

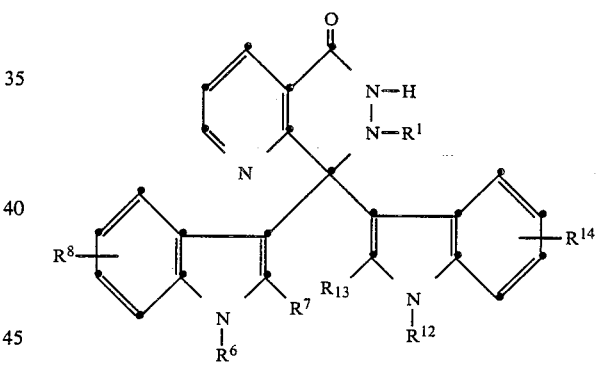

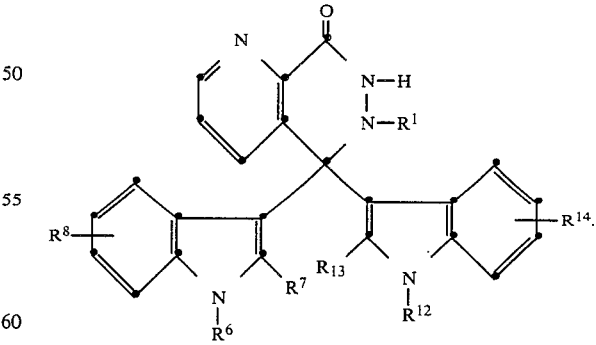

in which R¹, R⁶, R⁷, R⁸, R¹², R¹³ and R¹⁴ each have the same respective meanings given in claim 7.

10. A substrate for use in electrochromic recording comprising a support sheet containing as a color-forming substance a 2-(N-R¹-amino)-3-X-3-Y-R-phthalimidine having the structural formula

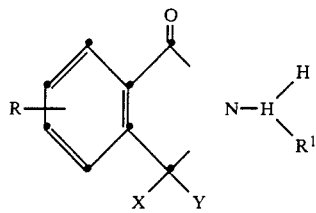

wherein:
R represents hydrogen, dialkylamino in which alkyl is non-tertiary $C_1$ to $C_4$ alkyl, $COOR^2$ in which $R^2$ is hydrogen or non-tertiary $C_1$ to $C_{16}$ alkyl or one to four halo;
$R^1$ represents hydrogen, $C_1$ to $C_3$ alkyl, pyridyl,

CZ in which Z is non-tertiary $C_1$ to $C_4$ alkoxy, $NHNH_2$, or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino;
X is selected from the group consisting of

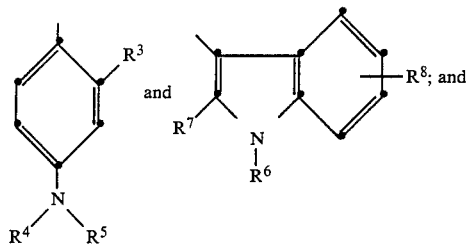

Y is selected from the group consisting of hydrogen,

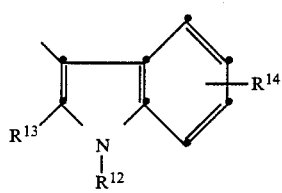

in which
$R^3$ selects hydrogen, non-tertiary $C_1$ to $C_4$ alkyl, non-tertiary $C_1$ $C_4$ alkoxy, acylamido in which acyl is non-tertiary $C_2$ to $C_4$ alkyl or dialkylamino in which alkyl is non-tertiary $C_1$ to $C_4$ alkyl,
$R^4$ represents non-tertiary $C_1$ to $C_4$ alkyl, benzyl or benzyl substituted in the benzene ring by one or two of halo or $C_1$ to $C_3$ alkyl,
$R^5$ represents non-tertiary $C_1$ to $C_4$ alkyl, benzyl or benzyl substituted in the benzene ring by one or two of halo or $C_1$ to $C_3$ alkyl,
$R^6$ and $R^{12}$ independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or $C_1$ to $C_3$ alkyl,
$R^7$ and $R^{13}$ independently represent hydrogen, $C_1$ to $C_3$ alkyl or phenyl, and $R^8$ and $R^{14}$ independently represent hydrogen, halo, non-tertiary $C_1$ to $C_4$ alkyl, non-tertiary $C_1$ to $C_4$ alkoxy or nitro.

11. A substrate for use in electrochromic recording according to claim 10 comprising a support sheet containing as a color-forming substance a 2-(N-$R^1$-amino)-3-[2-$R^3$-4-(N-$R^4$-N-$R^5$-amino)phenyl]-R-phthalimidine having the structural formula

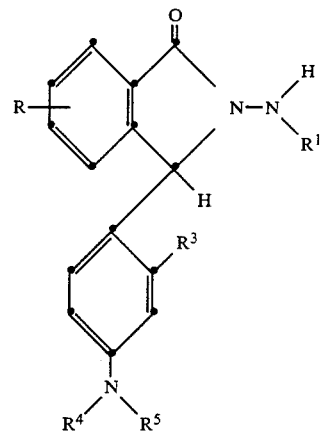

in which R, $R^1$, $R^3$, $R^4$ and $R^5$ each have the same respective meanings given in claim 3.

12. A substrate for use in electrochromic recording according to claim 10 comprising a support sheet containing as a color-forming substance a 2-(N-$R^1$-amino)-3-[2-$R^3$-4-(N-$R^4$-N-$R^5$-amino)phenyl]-3-(1-$R^{12}$-2-$R^{13}$-5/6-$R^{14}$-indol-3-yl)-R-phthalimidine having the structural formula

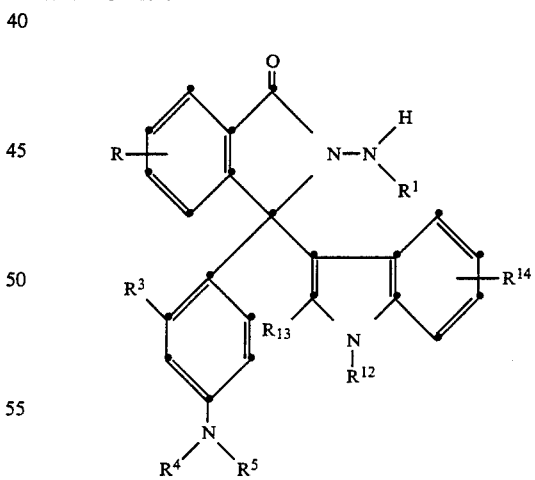

in which R, $R^1$, $R^3$, $R^4$, $R^5$, $R^{12}$, $R^{13}$ and $R^{14}$ each have the same respective meanings given in claim 10.

13. A substrate for use in electrochromic recording according to claim 10 comprising a support sheet containing as a color-forming substance a 2-(N-$R^1$-amino)-3-(1-$R^6$-2-$R^7$-5/6-$R^8$-indol-3-yl)-3-(1-$R^{12}$-2-$R^{13}$-5/6-$R^{14}$-indol-3-yl)-R-phthalimidine having the structural formula in which R, $R^1$, $R^6$, $R^7$, $R^8$, $R^{12}$, $R^{13}$ and $R^{14}$ each have the same respective meanings given in claim 10.

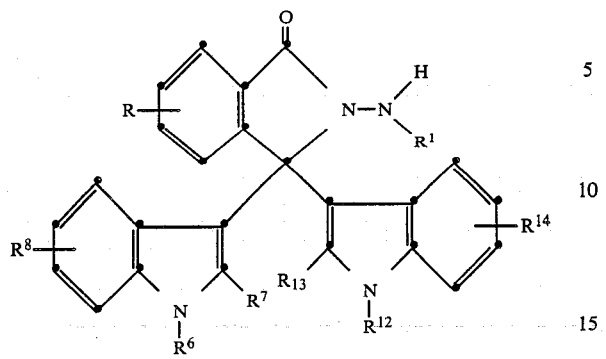

14. A substrate for use in electrochromic recording comprising a support sheet containing as color-forming substances an isomeric mixture of 6-(N-$R^1$-amino)-7-X-7-Y-(5H)-pyrrolo-[3,4-b]-pyridin-5-ones and 5-X-5-Y-6-(N-$R^1$-amino)-(7H)-pyrrolo-[3,4-b]-pyridin-7-ones having the structural formulas

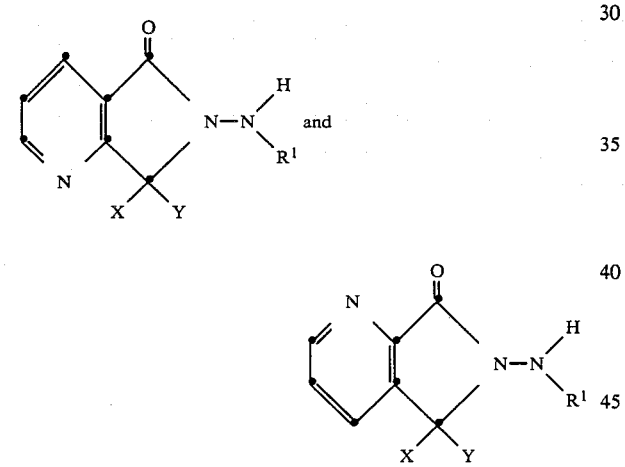

wherein:
R represents hydrogen, dialkylamino in which alkyl is non-tertiary $C_1$ to $C_4$ alkyl, $COOR^2$ in which $R^2$ is hydrogen or non-tertiary $C_1$ to $C_{16}$ alkyl or one to four halo;

$R^1$ represents hydrogen, $C_1$ to $C_3$ alkyl, pyridyl,

CZ in which Z is non-tertiary $C_1$ to $C_4$ alkoxy, $NHNH_2$, or non-tertiary $C_1$ to $C_4$ alkyl, phenyl or phenyl substituted by one or two of $C_1$ to $C_3$ alkyl, non-tertiary $C_1$ to $C_4$ alkoxy, halo, nitro or amino;

X is selected from the group consisting of

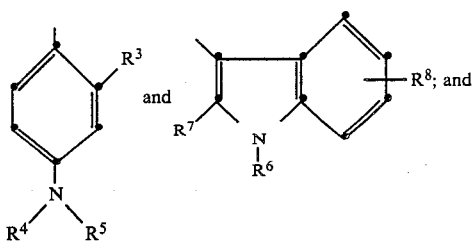

Y is selected from the group consisting of hydrogen,

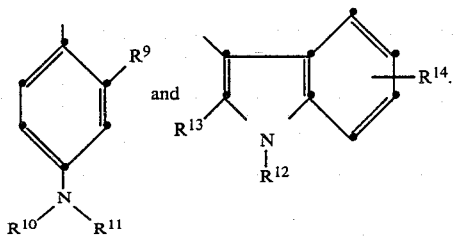

in which
$R^3$ and $R^9$ independently represent hydrogen, non-tertiary $C_1$ to $C_4$ alkyl, non-tertiary $C_1$ to $C_4$ alkoxy, acylamido in which acyl is non-tertiary $C_2$ to $C_4$ alkyl or dialkylamino in which alkyl is non-tertiary $C_1$ to $C_4$ alkyl, $R^4$ and $R^{10}$ independently represent non-tertiary $C_1$ to $C_4$ alkyl, benzyl or benzyl substituted in the benzene ring by one or two of halo or $C_1$ to $C_3$ alkyl, $R^5$ and $R^{11}$ independently represent non-tertiary $C_1$ to $C_4$ alkyl, benzyl or benzyl substituted in the benzene ring by one or two of halo or $C_1$ to $C_3$ alkyl, $R^6$ and $R^{12}$ independently represent hydrogen, non-tertiary $C_1$ to $C_{16}$ alkyl, non-tertiary $C_2$ to $C_8$ alkylene, phenoxyethyl, benzyl or benzyl substituted in the benzene ring by one or two of halo or $C_1$ to $C_3$ alkyl, $R^7$ and $R^{13}$ independently represent hydrogen, $C_1$ to $C_3$ alkyl or phenyl, and $R^8$ and $R^{14}$ independently represent hydrogen, halo, non-tertiary $C_1$ to $C_4$ alkyl, non-tertiary $C_1$ to $C_4$ alkoxy or nitro.

15. A substrate for use in electrochromic recording according to claim 14 comprising a support sheet containing as color-forming substances an isomeric mixture of 6-(N-$R^1$-amino)-7-[2-$R^3$-4-(N-$R^4$-N-$R^5$-amino)-phenyl]-7-(1-$R^{12}$-2-$R^{13}$-5/6-$R^{14}$-indol-3-yl)-(5H)-pyrrolo-[3,4-b]-pyridin-5-ones and 5-[2-$R^3$-4-(N-$R^4$-N-$R^5$-amino)phenyl]-5-(1-$R^{12}$-2-$R^{13}$-5/6-$R^{14}$-indol-3-yl)-6-(N-$R^1$-amino)-(7H)-pyrrolo-[3,4-b]-pyridin-7-ones having the structural formulas

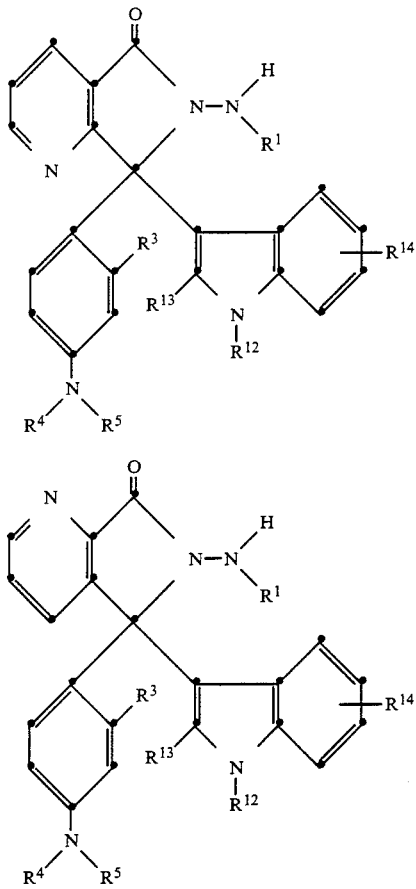

in which N, $R^1$, $R^3$, $R^4$, $R^5$, $R^{12}$, $R^{13}$ and $R^{14}$ each have the same respective meanings given in claim 14.

16. A substrate for use in electrochromic recording according to claim 14 comprising a support sheet containing as color-forming substances an isomer mixture of 6-(N-$R^1$-amino)-7-(1-$R^6$-2-$R^7$-5/6-$R^8$-indol-3-yl)-7-(1-$R^{12}$-2-$R^{13}$-5/6-$R^{14}$-indol-3-yl)-(5H)-pyrrolo-[3,4-b]-pyridin-5-ones and 5-(1-$R^6$-2-$R^7$-5/6-$R^8$-indol-3-yl)-5-(1-$R^{12}$-2-$R^{13}$-5/6-$R^{14}$-indol-3-yl)-6-(N-$R^1$-amino)-(7H)-pyrrolo-[3,4-b]-pyridin-7-ones having the structural formulas

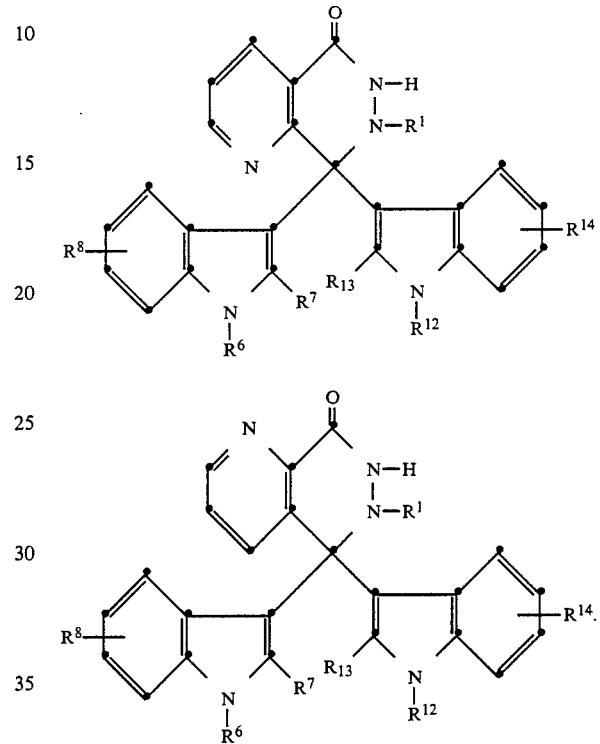

in which $R^1$, $R^6$, $R^7$, $R^8$, $R^{12}$, $R^{13}$ and $R^{14}$ each have the same respective meanings given in claim 14.

* * * * *

UNITED STATES PATENT AND TRADEMARK OFFICE
CERTIFICATE OF CORRECTION

PATENT NO. : 4,539,579

DATED : September 3, 1985

INVENTOR(S) : Paul J. Schmidt & William M. Hung

It is certified that error appears in the above-identified patent and that said Letters Patent is hereby corrected as shown below:

Cover page, U.S. PATENT DOCUMENTS, "Fujiuara" should read --Fujiwara--.

Column 54, lines 30-39, Claim 7, left-hand formula should read

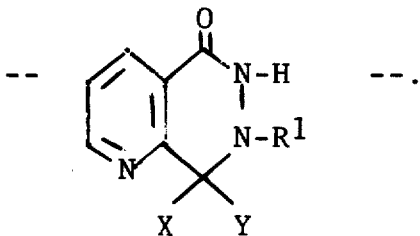

Column 56, line 27, Claim 9, "[P2,3d]" should read --[2,3d]--.

Column 57, line 52, Claim 10, "$R^3$ selects" should read --$R^3$ represents--; line 53, Claim 10, "$C_1$ $C_4$" should read --$C_1$ to $C_4$--.

UNITED STATES PATENT AND TRADEMARK OFFICE
CERTIFICATE OF CORRECTION

PATENT NO. : 4,539,579

DATED : September 3, 1985

INVENTOR(S) : Paul J. Schmidt & William M. Hung

It is certified that error appears in the above-identified patent and that said Letters Patent is hereby corrected as shown below:

Column 58, line 31, Claim 11, "given in claim 3" should read --given in claim 10--.

Column 61, line 41, Claim 16, "isomer" should read --isomeric--.

Signed and Sealed this

Eleventh Day of November, 1986

*Attest:*

DONALD J. QUIGG

*Attesting Officer*   *Commissioner of Patents and Trademarks*